United States Patent
Zisow

(10) Patent No.: US 8,628,468 B2
(45) Date of Patent: Jan. 14, 2014

(54) DEVICE FOR ANCHORING A TROCAR

(76) Inventor: David L. Zisow, Baltimore, MD (US)

( * ) Notice: Subject to any disclaimer, the term of this patent is extended or adjusted under 35 U.S.C. 154(b) by 34 days.

(21) Appl. No.: 13/168,586

(22) Filed: Jun. 24, 2011

(65) Prior Publication Data

US 2011/0319826 A1    Dec. 29, 2011

Related U.S. Application Data

(63) Continuation-in-part of application No. 12/233,538, filed on Oct. 1, 2008, now abandoned.

(51) Int. Cl.
*A61B 17/34* (2006.01)
*A61B 1/00* (2006.01)

(52) U.S. Cl.
USPC .......................................... 600/184; 606/185

(58) Field of Classification Search
USPC .......... 606/185, 108, 184; 600/114, 115, 127, 600/129, 184, 201; 604/164.01, 164.03, 604/164.04, 164.08
See application file for complete search history.

(56) References Cited

U.S. PATENT DOCUMENTS

| 3,717,151 A | 2/1973 | Collett |
| 4,574,806 A | 3/1986 | McCarthy |
| 4,931,042 A | 6/1990 | Holmes et al. |
| 5,066,288 A | 11/1991 | Deniega et al. |
| 5,147,316 A | 9/1992 | Castillenti |
| 5,176,127 A | 1/1993 | Dormia |
| 5,203,773 A | 4/1993 | Green |
| 5,232,451 A | 8/1993 | Freitas et al. |
| 5,248,302 A | 9/1993 | Patrick et al. |
| 5,279,564 A | 1/1994 | Taylor |
| 5,350,393 A | 9/1994 | Yoon |
| 5,354,302 A | 10/1994 | Ko |
| 5,366,445 A | 11/1994 | Haber et al. |
| 5,387,197 A | 2/1995 | Smith et al. |
| 5,391,156 A | 2/1995 | Hildwein et al. |
| 5,569,289 A | 10/1996 | Yoon |
| 5,785,707 A * | 7/1998 | Boyd et al. ...................... 606/41 |
| 5,817,062 A * | 10/1998 | Flom et al. .................... 604/174 |
| 5,931,776 A * | 8/1999 | Dotolo .......................... 600/184 |
| 5,971,960 A | 10/1999 | Flom et al. |
| 6,447,444 B1 * | 9/2002 | Avni et al. ..................... 600/121 |
| 6,589,214 B2 | 7/2003 | McGuckin, Jr. et al. |
| 6,673,058 B2 | 1/2004 | Snow |
| 7,422,572 B2 | 9/2008 | Popov et al. |
| 7,708,713 B2 | 5/2010 | Albrecht et al. |

(Continued)

FOREIGN PATENT DOCUMENTS

EP    614646    9/1994

*Primary Examiner* — Elizabeth Houston
(74) *Attorney, Agent, or Firm* — Plumsea Law Group, LLC

(57) ABSTRACT

A device for anchoring a trocar is disclosed. The device may include a spacer and a device having a main body and a device sleeve. A device tip may be hingedly connected to a distal end of the device sleeve. The spacer and the device may be configured to be assembled together with a trocar and an obturator. The spacer may provide distance between the device tip and an open distal end of the trocar sleeve when the obturator, trocar, spacer, and device are assembled together. Once the assembled parts are inserted into a body cavity the obturator, trocar, and spacer may be removed. Inside the body cavity, the device sleeve may receive the trocar sleeve. As the trocar sleeve progresses through the device sleeve, the open distal end of the trocar sleeve may push the device tip from a first position to a second position, anchoring the device.

20 Claims, 19 Drawing Sheets

(56) References Cited

U.S. PATENT DOCUMENTS

| | | |
|---|---|---|
| 7,731,692 B2 | 6/2010 | Moos et al. |
| 7,874,981 B2 * | 1/2011 | Whitman et al. ............ 600/184 |
| 8,206,411 B2 * | 6/2012 | Thompson et al. ........... 606/185 |
| 2005/0209619 A1 | 9/2005 | Johnson et al. |
| 2009/0182279 A1 | 7/2009 | Wenchell et al. |
| 2010/0081994 A1 | 4/2010 | Zisow |
| 2010/0210998 A1 | 8/2010 | Albrecht et al. |
| 2010/0217152 A1 | 8/2010 | Moos et al. |
| 2010/0312261 A1 | 12/2010 | Suzuki et al. |
| 2010/0324579 A1 | 12/2010 | Bardy |

* cited by examiner

DEVICE FOR ANCHORING A TROCAR

CROSS-REFERENCE TO RELATED APPLICATION(S)

This application is a continuation-in-part of U.S. patent application Ser. No. 12/233,538 filed on Oct. 1, 2008, and published as U.S. Patent Publication Number 2010/0081994, the entirety of which is hereby incorporated by reference.

BACKGROUND OF THE INVENTION

Laparoscopic minimally invasive surgery has been rapidly developing. During this type of surgery, internal body parts may be viewed via an endoscopic camera attached to a laparoscope with the image transmitted to a monitor screen. Entry into the abdomen (and other body sites) is generally obtained via devices known as laparoscopic trocars. FIGS. 1 and 2 illustrate an example of a conventional laparoscopic trocar 100. Trocar 100 may include a cylindrical sleeve 102 having an open distal end 118. Sleeve 102 may provide a route for accessing a body cavity through a small incision. Sleeve 102 may also provide a passage for carbon dioxide gas to be pumped into the body cavity to distend the body cavity, providing better visibility within the body cavity.

An obturator 106 may be used with trocar 100 to insert trocar 100 into the body cavity. Obturator 106 may include a tube 120 having a pointed tip 110 at a distal end. Pointed tip 110 may include a first separator 114 and a second separator 116. An obturator main body 108 may be attached to obturator 106 at a proximal end. Trocar 100 may include a trocar main body 112 attached to a proximal end of sleeve 102. As shown in FIG. 2, obturator 106 may be assembled with trocar 100 by inserting tube 120 through trocar main body 112 into sleeve 102. Pointed tip 110 may protrude through the distal end of sleeve 102. Assembled together, obturator 106 and trocar 100 may be inserted into a body cavity through an incision made by a scalpel. Pointed tip 110 may penetrate through tissue as obturator 106 and trocar 100 are pushed and twisted into the body cavity. First separator 114 and second separator 116 may help separate tissue as obturator 106 and trocar 100 are pressed into the body cavity. Once trocar 100 is in place, obturator 106 may be removed from trocar 100 so that surgical instruments may be introduced into the body cavity through sleeve 102.

If trocar 100 is accidentally dislodged from its placement site surgical instruments cannot be placed into the body cavity. Dislodgement slows down the operative procedure while the surgeon struggles to return trocar 100 to the body cavity. Furthermore, in the event of dislodgment, the carbon dioxide gas used to distend the body cavity during such procedures dissects into the subcutaneous tissue spaces because trocar 100 is no longer preventing same. Due to all of these problems, avoidance of trocar displacement is a critical aspect of successful laparoscopic surgery. To help prevent trocar displacement, the outer surface of sleeve 102 may include ridges 104. Ridges 104 are intended to help retain trocar 100 within the incision by friction between the body wall tissues and ridges 104. However, this amount of friction does not always prevent trocar 100 from dislocating itself or slipping out from the body. For example, when a surgical instrument is quickly removed from trocar 100 during an emergency, the surgical instrument may be removed with the distal end of the instrument inadvertently left in a position that causes the distal end to not fit through sleeve 102. In this position, the distal end of the instrument may press against the distal end of sleeve 102 forcing sleeve 102 to be displaced. Because of the problems associated with trocar displacement, it would be advantageous for a system and method for preventing trocar displacement.

SUMMARY OF THE INVENTION

A device and method for more securely anchoring a trocar within a body cavity is disclosed. Prevention of trocar displacement is an important aspect of successful laparoscopic surgery. In a critical moment during a laparoscopic surgery, precious time may be lost while trying to reposition or reinsert the trocar after trocar displacement. Thus, anchoring a trocar in place may prevent damage caused during the time needed to reposition or reinsert a displaced trocar.

In one aspect, the system may include a device main body and a device sleeve extending from the device main body. The device sleeve may have a proximal end and an open distal end. A hole may extend through the device main body and the device sleeve. A device tip may have a proximal end configured to be retained by the open distal end of the device sleeve and a distal end opposite the proximal end. A device tip may be hingedly connected to the open distal end of the device sleeve such that the device tip may be moved from a first position, in which the distal end of the device tip is directed downward away from the proximal end of the sleeve, to a second position, in which the distal end of the device tip is directed may point laterally with respect to the longitudinal axis of the device sleeve.

In another aspect, the system may include a device main body having a top surface or portion and a bottom surface or portion opposite the top surface or portion. A device sleeve may extend from the bottom portion. The device sleeve may have a proximal end and an open distal end. A hole may extend through the device main body and the device sleeve. The hole may be configured to receive an obturator tube. The proximal end of the device tip may be configured to receive a substantially cone-shaped obturator tip disposed on a distal end of an obturator tube. The proximal end of the device tip may have a shape corresponding to the shape of the obturator tip.

In another aspect, the system may include a device having a device main body. The device main body may have a device top portion and a device bottom portion opposite the device top portion. The device top portion may be configured to receive a trocar main body. A device sleeve may extend from the device bottom portion of the device main body. The device sleeve may have a proximal end and an open distal end opposite the proximal end. The device main body may define an aperture that is in communication with the device sleeve, the aperture and sleeve providing a passageway into which a trocar may be received. That is, a device hole or aperture may extend through the device main body and the device sleeve. The device hole may be configured to receive a trocar sleeve. A device tip may have a proximal end configured to be retained by the open distal end of the device sleeve. The device tip may be in a first position when retained by the open distal end of the device sleeve. A hinge may connect the proximal end of the device tip to the open distal end of the device sleeve. The hinge may enable the device tip to pivot from the first position to a second position.

Other systems, methods, features and advantages of the invention will be, or will become, apparent to one of ordinary skill in the art upon examination of the following figures and detailed description. It is intended that all such additional systems, methods, features and advantages be included within this description and this summary, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DETAILED DESCRIPTION

Figure 1:
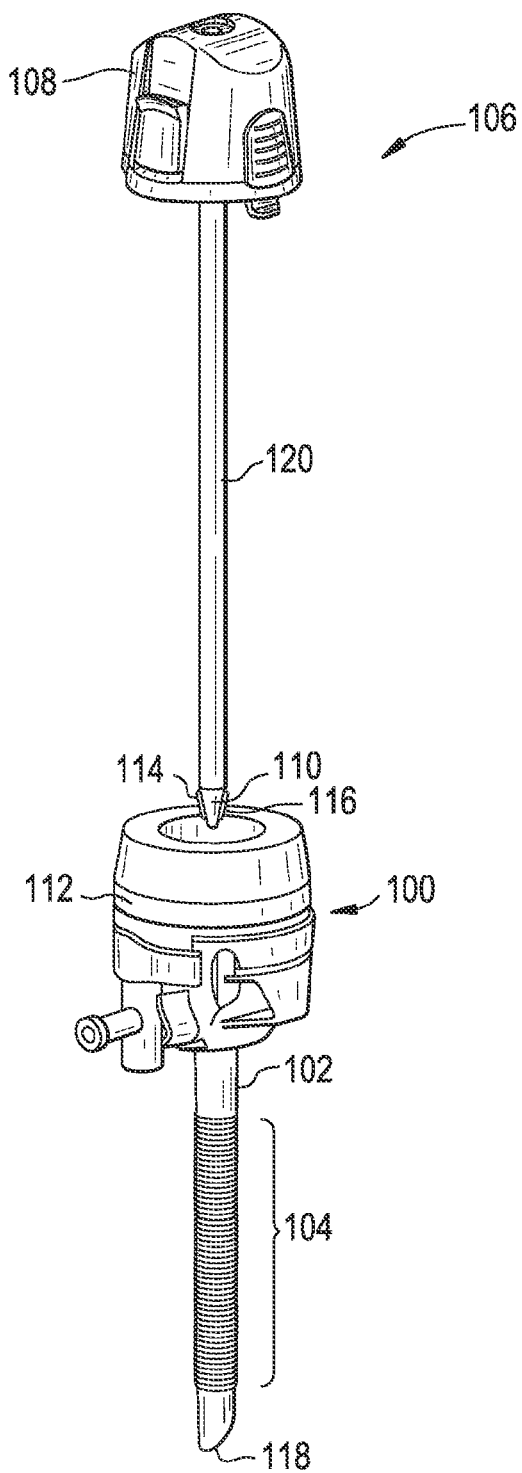
FIG. 1 illustrates a conventional obturator and trocar.
Figure 2:
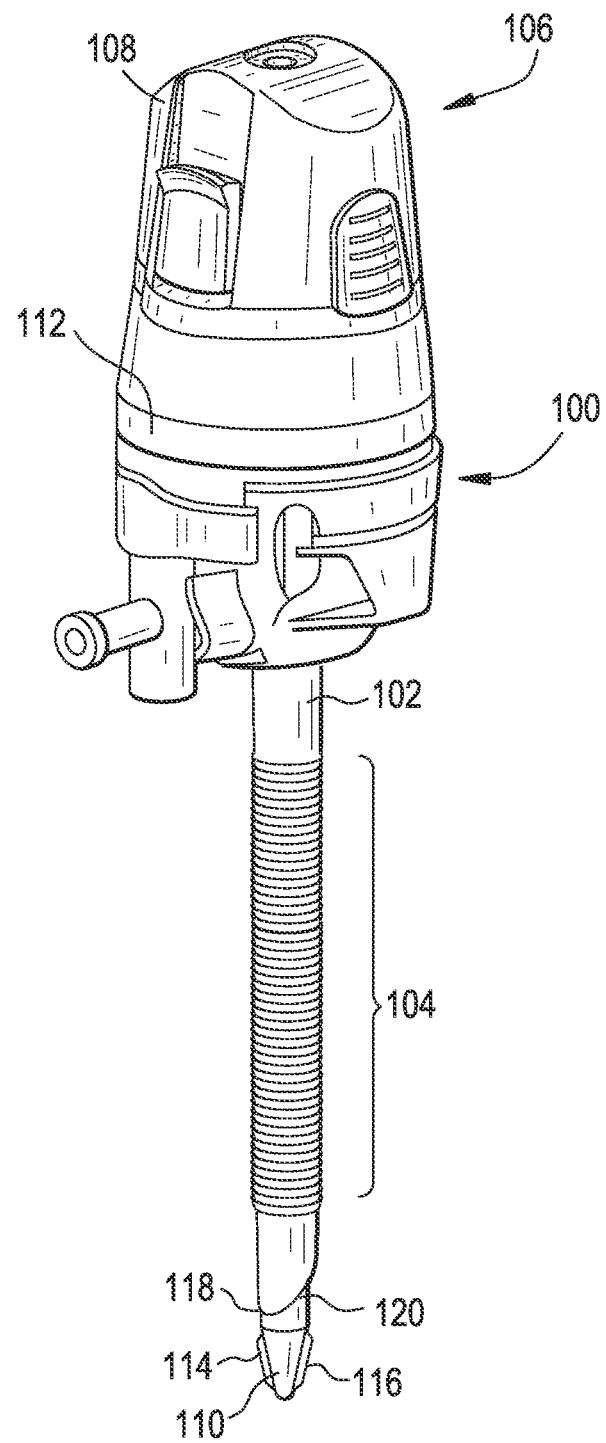
FIG. 2 illustrates the conventional obturator and trocar from FIG. 1 assembled together.
Figure 3:
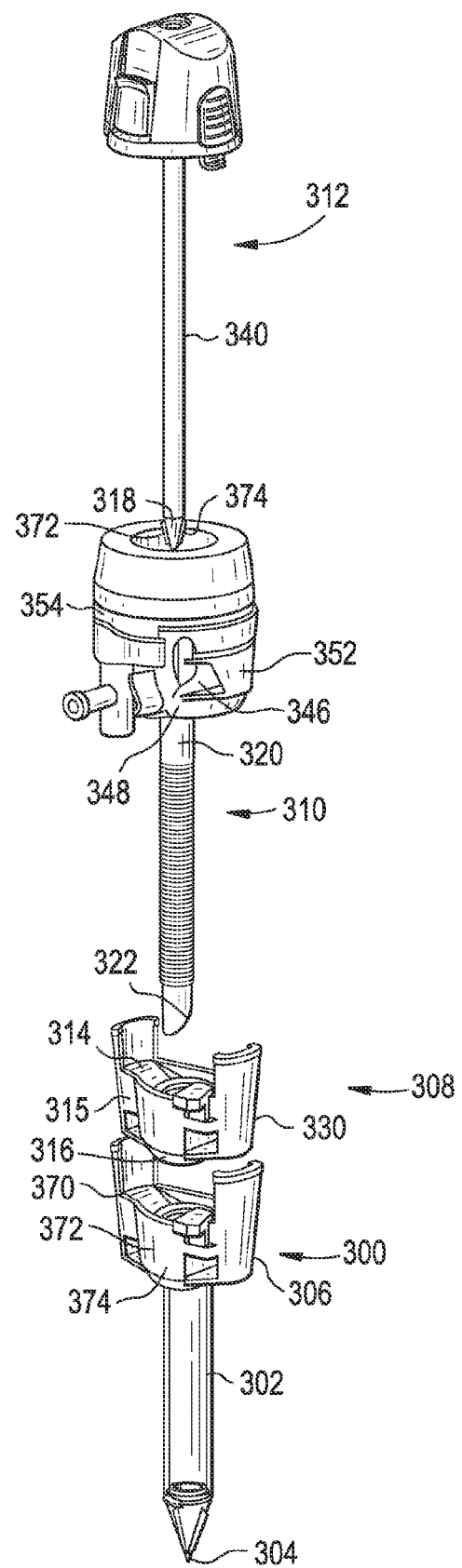
FIG. 3 illustrates an obturator and trocar aligned with a spacer and a device, according to an exemplary embodiment.
Figure 4:
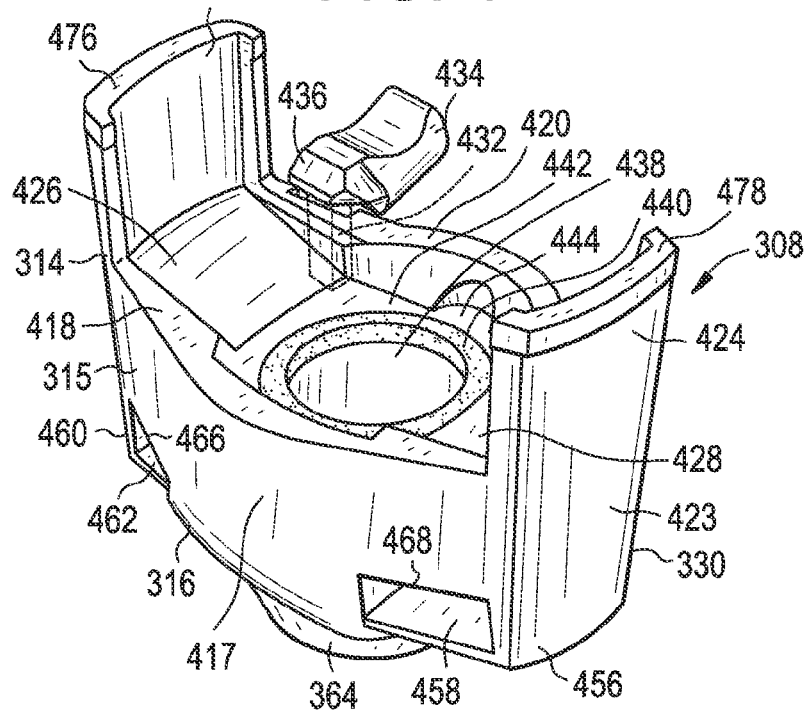
FIG. 4 is the spacer of the exemplary embodiment shown in FIG. 3 with a tab shown in a first position.

FIGS. 3-20 illustrate an exemplary embodiment of a system for anchoring a trocar. The system may include a device 300 having a device sleeve 302 with a device pointed tip 304 at a distal end and a device main body 306 at a proximal end. The system may further include a spacer 308. As discussed in more detail below, the system may be configured to be used with existing trocars. For example, as shown in the exemplary embodiment of FIGS. 3-14, the system may be configured to be used with a trocar 310 and an obturator 312. It should be understood that the system may be configured to be used with other types of existing trocars and/or obturators. The device does not replace a trocar, but is instead configured to connectedly receive a commercially available trocar. The connection between the device and the trocar may be achieved in any number of ways, and may depend upon the geometry and construction of the existing trocar.

Figure 16:
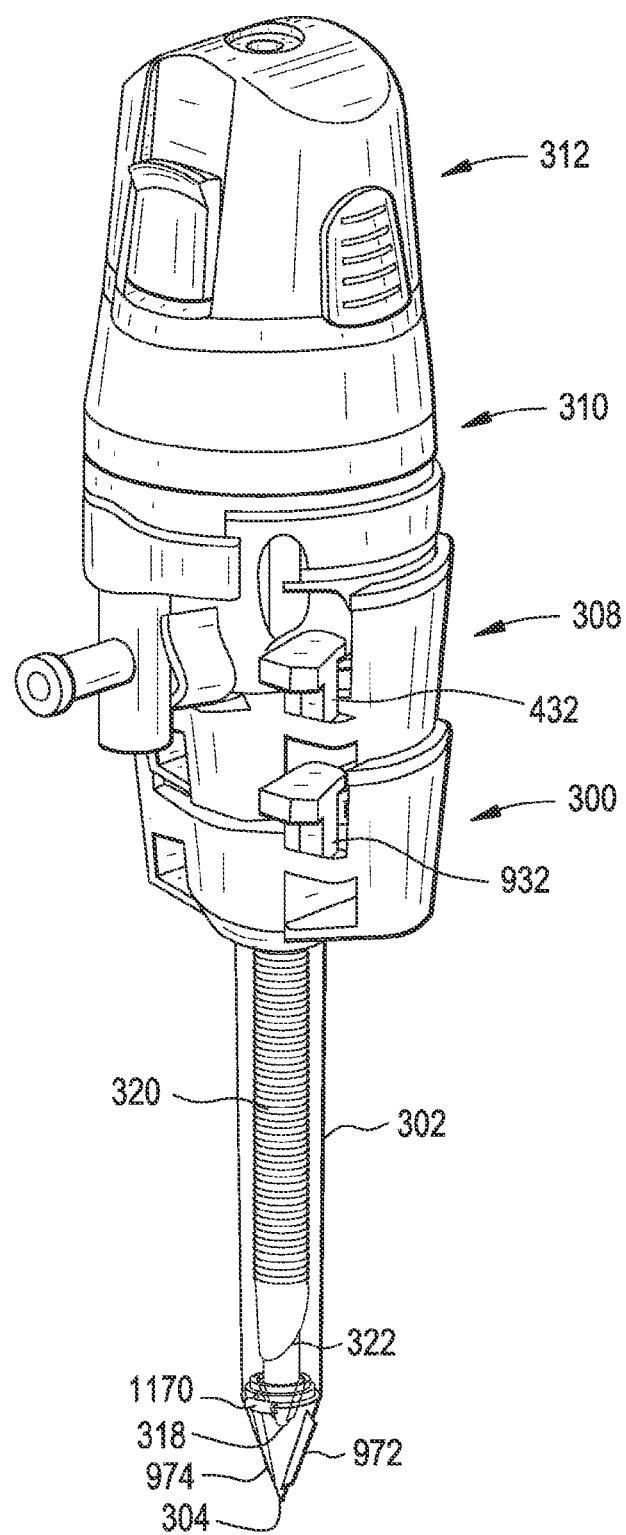
FIG. 16 is the obturator, trocar, spacer, and device of the exemplary embodiment shown in FIG. 3 assembled together.
Figure 17:
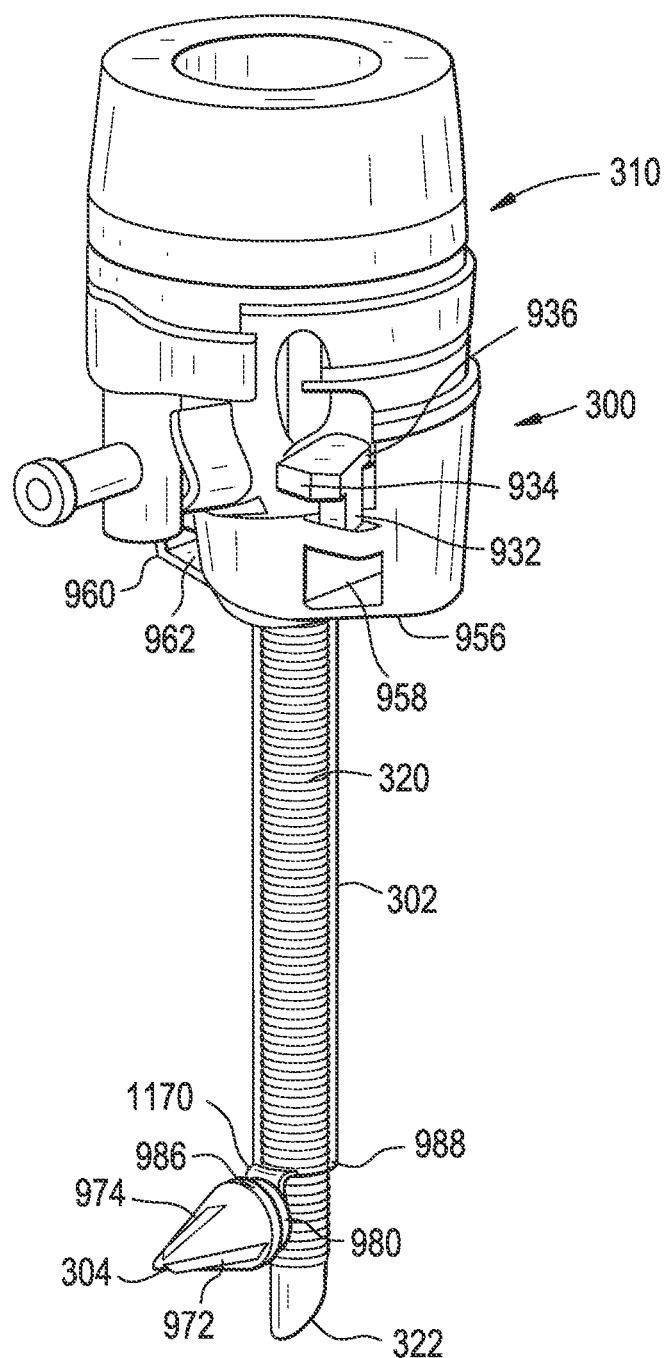
FIG. 17 is the trocar and the device of the exemplary embodiment shown in FIG. 3 assembled together.
Figure 18:
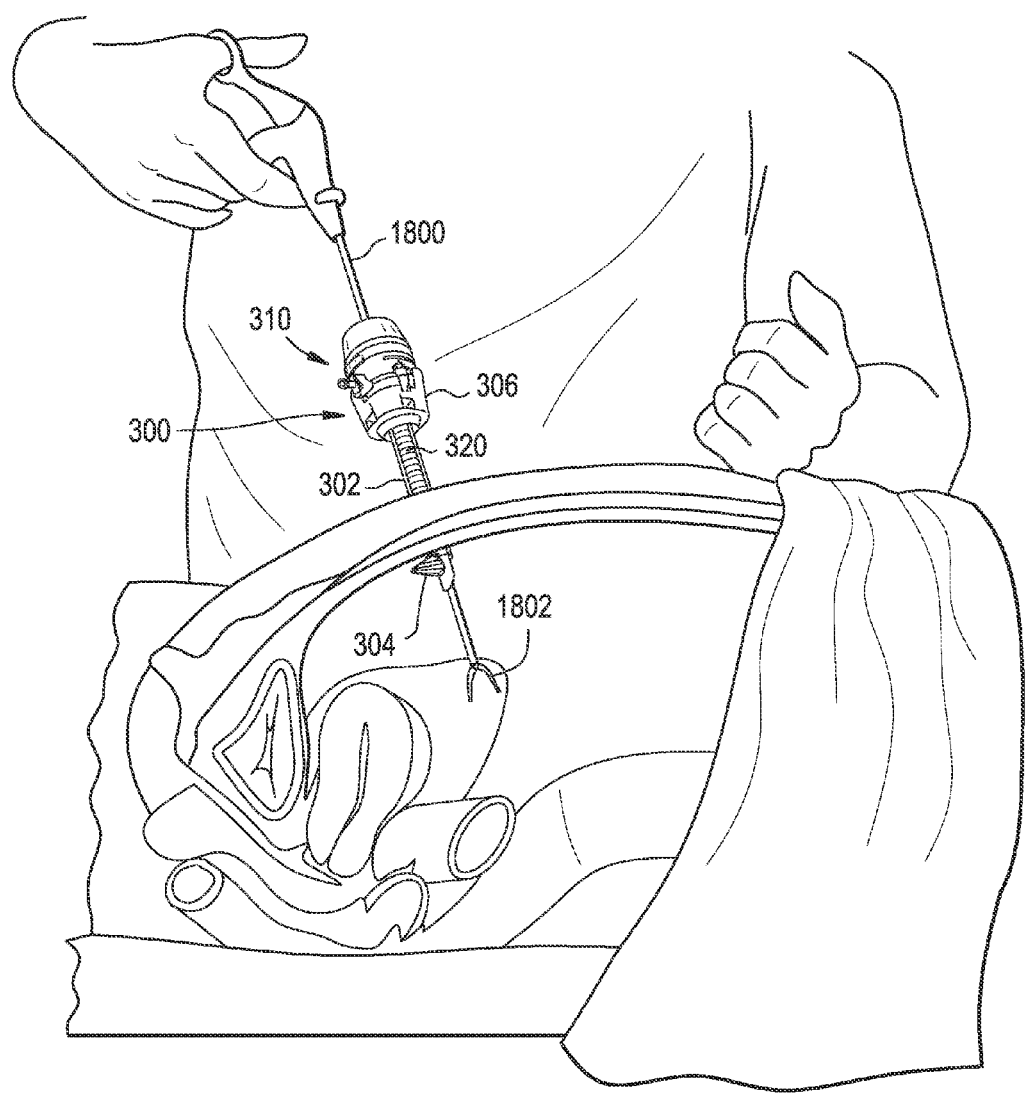
FIG. 18 is the trocar and the device of the exemplary embodiment shown in FIG. 3 assembled together and inserted inside a body cavity with a surgical instrument extending through the assembly.
Figure 19:
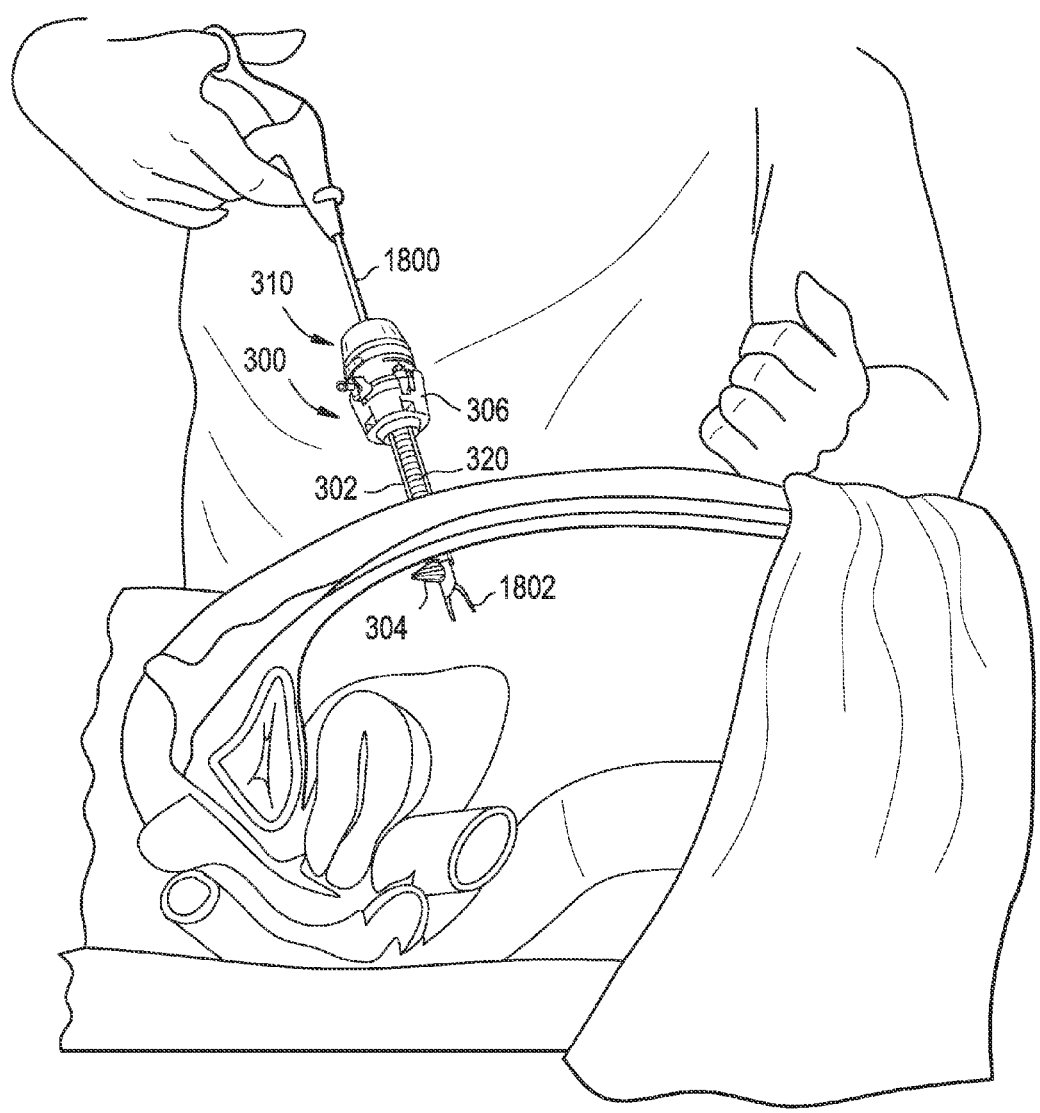
FIG. 19 is the trocar, device, and surgical instrument shown in FIG. 18 with a grasping end of the surgical instrument pressing upward against a device sleeve opening.
Figure 20:
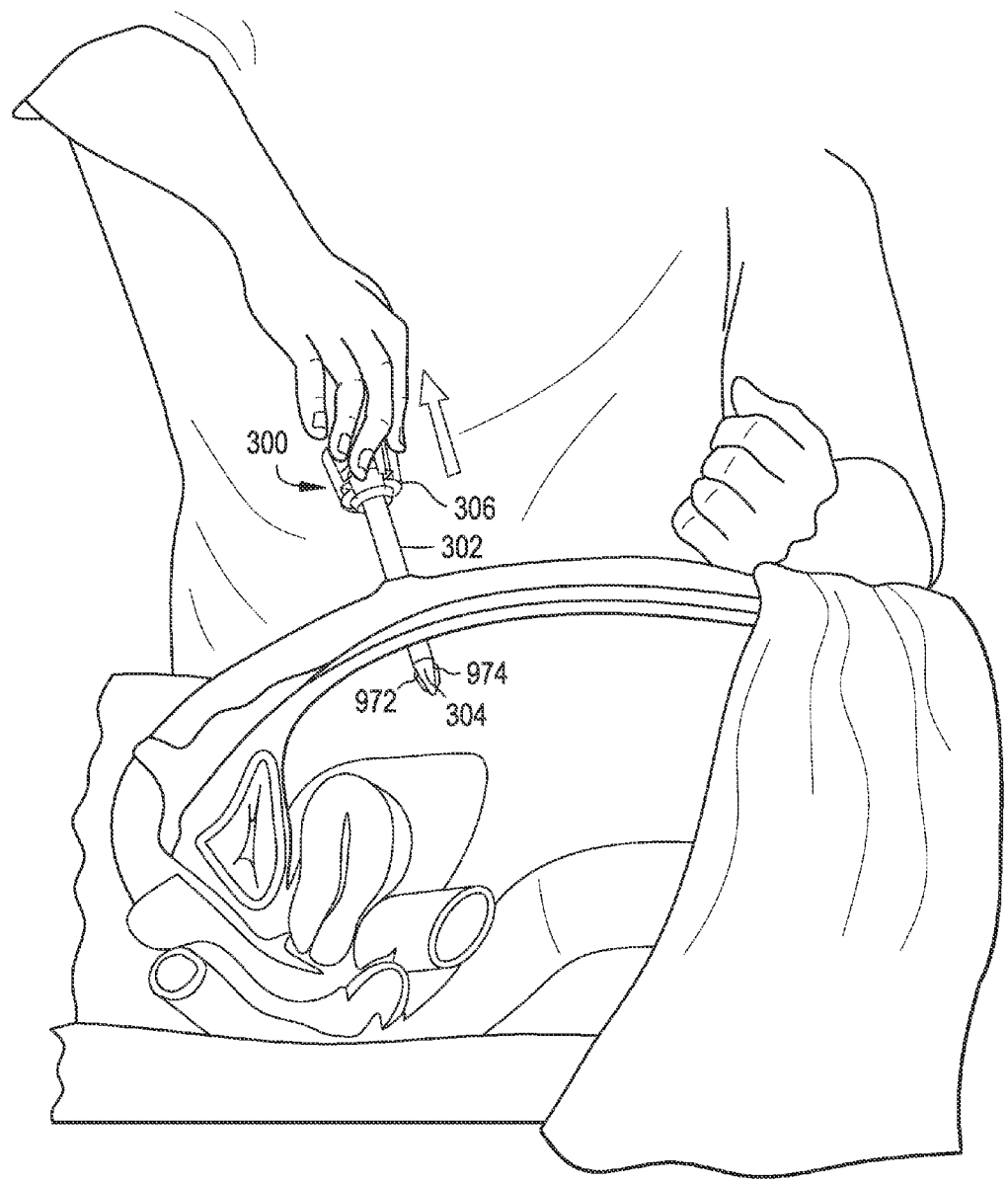
FIG. 20 is the device of the exemplary embodiment of FIG. 3 being pulled from the body cavity.

As shown in FIG. 16 and described in further detail below, device 300 and spacer 308 may be assembled with trocar 310 and obturator 312. In this assembly, device pointed tip 304 may be directed downward. This assembly may allow for insertion of device 300 and trocar 310 into a body cavity through an incision made by a scalpel. Once device 300 is in place within the body cavity, obturator 312, trocar 310, and spacer 308 may be removed from device 300. Then, trocar 310 may be inserted within device 300 such that a trocar sleeve 320 extends through device sleeve 302. Without spacer 308 increasing the distance between device 300 and trocar 310, trocar sleeve 320 may extend further inside device sleeve 302 such that trocar sleeve 320 pushes device pointed tip 304 out of device sleeve 302, as shown in FIG. 17 and described in further detail below. FIGS. 18 and 19 illustrate how device pointed tip 304 may anchor device 300 within the body cavity when device pointed tip 304 is directed laterally with respect to the longitudinal axis of device sleeve 302. Trocar sleeve 320 may prevent device pointed tip 304 from pointing downward. Once trocar is removed from device 300, device pointed tip 304 may no longer be prevented from pointing downward. When device 300 is pulled from the body cavity, tissue surrounding the incision and/or tissues inside the body cavity may push device pointed tip 304 downward such that device 300 may be removed from the body cavity (FIG. 20).

In some embodiments, spacer 308 may include a spacer main body 330 having a spacer top portion 314 and a spacer bottom portion 316. In some embodiments, spacer main body 330 may have a spacer middle portion 315 disposed between spacer top portion 314 and spacer bottom portion 316. In some embodiments, spacer middle portion 315 may include a first lateral surface 417 extending between spacer top portion 314 and spacer bottom portion 316. A second lateral surface 619 may oppose first lateral surface 417 in a position extending between spacer top portion 314 and spacer bottom portion 316. A third lateral surface 621 may extend between first lateral surface 417, second lateral surface 619, spacer top portion 314, and spacer bottom portion 316. A fourth lateral surface 423 may extend between first lateral surface 417, second lateral surface 619, spacer top portion 314, and spacer bottom portion 316. Fourth lateral surface 423 may oppose third lateral surface 621. In some embodiments, first lateral surface 417 may be substantially curved. In some embodiments, second lateral surface 619 may be substantially curved. In some embodiments, first lateral surface 417 and second lateral surface 619 may both be substantially curved so that the distance between first lateral surface 417 and second lateral surface 619 increases toward the middle of first lateral surface 417 and second lateral surface 619.

While the drawings illustrate a spacer having a configuration that is largely identical to the device main body, it is noted that this is not a requirement. The spacer may have a wholly different configuration and not resemble the device main body at all. The only requirement if a spacer is used is that its main body receives the trocar and also engages the main body of the anchoring device.

In some embodiments, first lateral surface 417 may be substantially wider than third lateral surface 621 and fourth lateral surface 423. In some embodiments, second lateral surface 619 may be substantially wider than third lateral surface 621 and fourth lateral surface 423. In some embodiments, first lateral surface 417 and second lateral surface 619 may have substantially the same width. In some embodiments, the width of first lateral surface 417, second lateral surface 619, third lateral surface 621, and/or fourth lateral surface 423 may be tapered toward spacer bottom portion 316 (see FIG. 6). The width, shape, and contour of first lateral surface 417, second lateral surface 619, third lateral surface 621, and/or fourth lateral surface 423 may be selected based on a variety of factors. For example, the width, shape, and contours of the lateral surfaces may be selected based on how spacer 308 may nest with device 300. In some embodiments, first lateral surface 417, second lateral surface 619, third lateral surface 621, and/or fourth lateral surface 423 may have the same height. In some embodiments, first lateral surface 417, second lateral surface 619, third lateral surface 621, and fourth lateral surface 423 may have different heights. The height of first lateral surface 417, second lateral surface 619, third lateral surface 621, and/or fourth lateral surface 423 may be selected based on a variety of factors. For example, the height of the lateral surfaces may be selected based on the length of trocar sleeve 320, the length of device sleeve 302, and/or the size of device main body 306.

In some embodiments, a spacer hole 438 may extend through spacer main body 330. Spacer hole 438 may extend through the center of spacer top portion 314, continuing through the center of spacer middle portion 315 and the center of spacer bottom portion 316. In some embodiments, spacer hole 438 may include any size and/or shape. For example, as shown in the exemplary embodiment of FIGS. 3-14, spacer hole 438 may be cylindrical. In some embodiments, spacer hole 438 may be configured to receive an obturator tube 340 and/or trocar sleeve 320. In some embodiments, the size and/or shape of spacer hole 438 may be selected based on a variety of factors. For example, in some embodiments, the size and/or shape of spacer hole 438 may be selected based on the size and/or shape of the tubes and sleeves spacer hole 438 is configured to receive.

In some embodiments, spacer top portion 314 may be configured to receive trocar main body 354. In some embodiments, spacer top portion 314 may be configured to receive a trocar bottom portion 346 of trocar main body 354. Spacer top portion 314 may have a shape corresponding to the shape of trocar bottom portion 346 of trocar main body 354. The size, shape, and/or contour of spacer top portion 314 may be selected based on a variety of factors. For example, size, shape, and/or contour of spacer top portion 314 may be selected based on the type of trocar main body used with the system.

In some embodiments, spacer top portion 314 may include a first top wall 418 disposed along a section of the perimeter of spacer top portion 314 and a second top wall 420 disposed along a section of the perimeter of spacer top portion 314 opposite first top wall 418. In some embodiments, an outer surface of first top wall 418 may coincide with first lateral surface 417. In some embodiments, an outer surface of second top wall 420 may coincide with second lateral surface 619. In some embodiments, an outer surface of third top wall 422 may coincide with third lateral surface 621. In some embodiments, an outer surface of fourth top wall 424 may coincide with fourth lateral surface 423.

In some embodiments, the section of the perimeter of spacer top portion 314 that is coincident with first top wall 418 may include a substantially curved shape. In some embodiments, the section of the perimeter of spacer top portion 314 that is coincident with second top wall 420 may include a substantially curved shape. In some embodiments, the sections of the perimeter of spacer top portion 314 that are coincident with first top wall 418 and second top wall 420 may both be substantially curved so that the distance between first top wall 418 and second top wall 420 increases toward the middle of first top wall 422 and second top wall 424 (see FIG. 7).

In some embodiments, a third top wall 422 may extend between first top wall 418 and second top wall 420. Third top wall 422 may be disposed along a section of the perimeter of spacer top portion 314. In some embodiments, a fourth top wall 424 may extend between first top wall 418 and second top wall 420. Fourth top wall 424 may be disposed along a section of the perimeter of spacer top portion 314. In some embodiments, fourth top wall 424 may oppose third top wall 422. In some embodiments, the section of the perimeter of spacer top portion 314 that is coincident with third top wall 422 may include a slightly curved shape. In some embodiments, the section of the perimeter of spacer top portion 314 that is coincident with second top wall 424 may include a slightly curved shape. In some embodiments, third top wall 422 and fourth top wall 424 may both be substantially taller than first top wall 418 and second top wall 420. In some embodiments, first top wall 418 and second top wall 420 may be substantially wider than both third top wall 422 and fourth top wall 424. In some embodiments, third top wall 422 may include a first flange 476 and fourth top wall 424 may include a second flange 478.

In some embodiments, spacer top portion 314 may be configured to receive a trocar bottom portion 346 of a trocar main body 354 such that trocar main body nests within the space between first top wall 418, second top wall 420, third top wall 422, and fourth top wall 424 (FIG. 16). In some embodiments, spacer 308 may be configured such that trocar bottom portion 346 of trocar main body 354 may fit flush within the space between first top wall 418, second top wall 420, third top wall 422, and fourth top wall 424.

In some embodiments, spacer top portion 314 may include a first sloped surface 426 and a second sloped surface 428 opposing first sloped surface 426. First sloped surface 426 may be disposed between first top wall 418, second top wall 420, third top wall 422, and spacer hole 438. Second sloped surface 428 may be disposed between first top wall 418, second top wall 420, fourth top wall 424, and spacer hole 438. In some embodiments, first sloped surface 426 and second sloped surface 428 may both decline toward the center of spacer top portion 314. In some embodiments, first sloped surface 426 and second sloped surface 428 may both include flat surfaces declining toward the center of spacer top portion 314.

In some embodiments, first sloped surface 426 may be configured to receive a first trocar angled wall 352 disposed on trocar bottom portion 346. In some embodiments, second sloped surface 428 may be configured to receive a second trocar angled wall (not shown), which is a mirror image of the first trocar angled wall 352. In some embodiments, third top wall 422 and fourth top wall 424 may be configured to receive trocar bottom portion 346. In some embodiments, third top wall 422 may be configured to receive a first trocar angled wall 352 disposed on trocar bottom portion 346. In some embodiments, fourth top wall 424 may be configured to receive the second trocar angled wall (not shown) of trocar main body 354.

In some embodiments, a washer space may surround spacer hole 438. Washer space may be configured to receive a washer 440 surrounding spacer hole 438. In some embodiments, the washer space may include an annular groove having a shape corresponding to the shape of washer 440. In some embodiments, washer 440 may be configured to seal the area between a trocar sleeve 320 and spacer hole 438 when trocar 310 is assembled with spacer 308.

In some embodiments, a recessed area 442 may surround the washer space. In some embodiments, recessed area 442 may be configured to receive trocar bottom portion 346. In some embodiments, recessed area 442 may include a surface declining toward the washer space. In some embodiments, recessed area 442 may include a flat surface. In some embodiments, recessed area 442 may be disposed between first sloped surface 426 and second sloped surface 428. In some embodiments, recessed area 442 may be disposed between first top wall 418 and second top wall 420. In some embodiments, recessed area 442 may be configured to correspond with a substantially cup-shaped area 348 on trocar bottom portion 346. In some embodiments, recessed area 442 may include a semicircular nook 444. In some embodiments, semicircular nook 444 may be configured to correspond with a semicircular protrusion disposed on trocar bottom portion 346.

Figure 5:
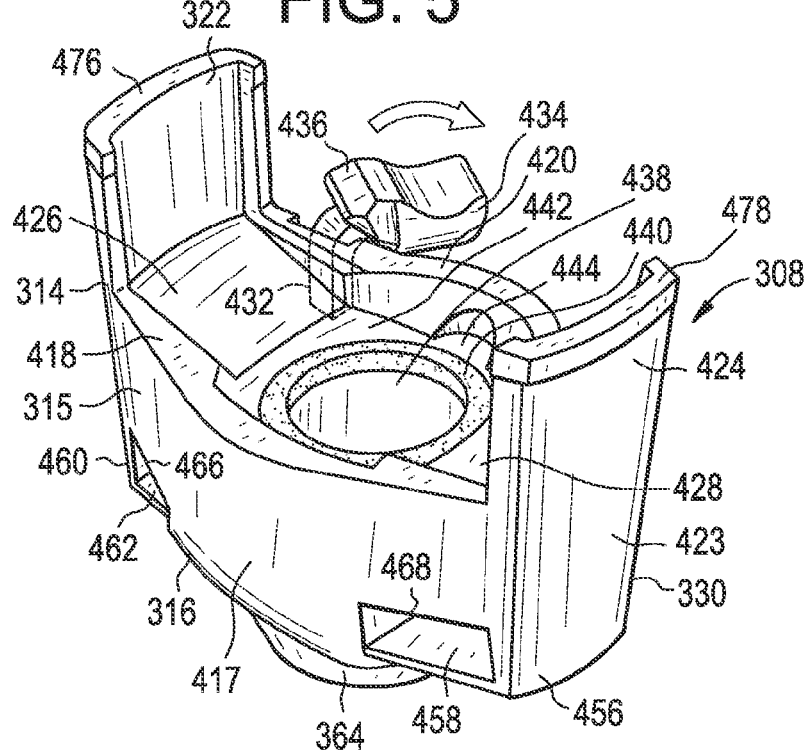
FIG. 5 is the spacer of the exemplary embodiment shown in FIG. 3 with the tab shown in a second position.
Figure 6:
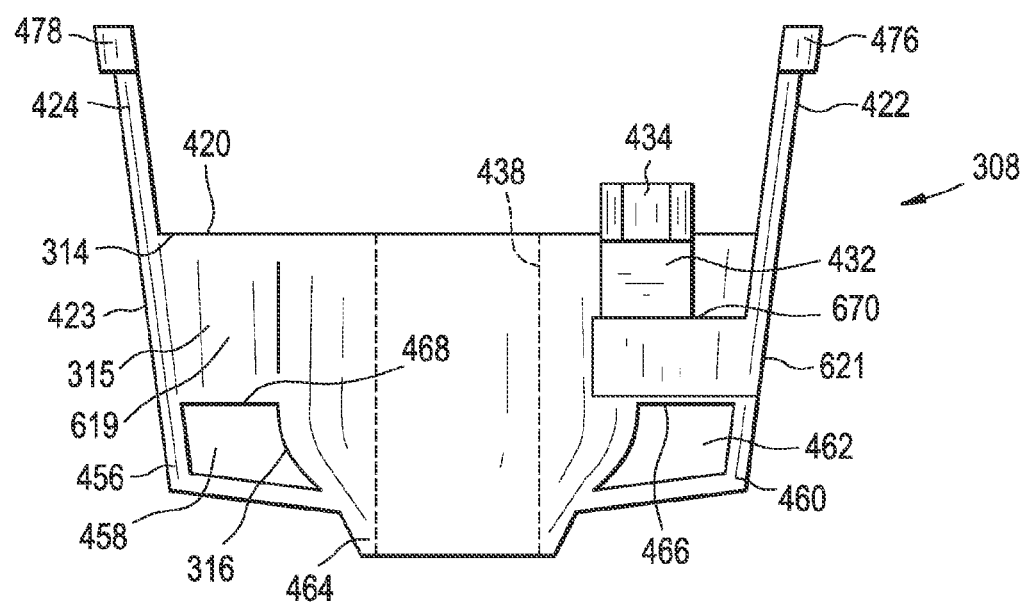
FIG. 6 is the spacer of the exemplary embodiment shown in FIG. 3.
Figure 7:
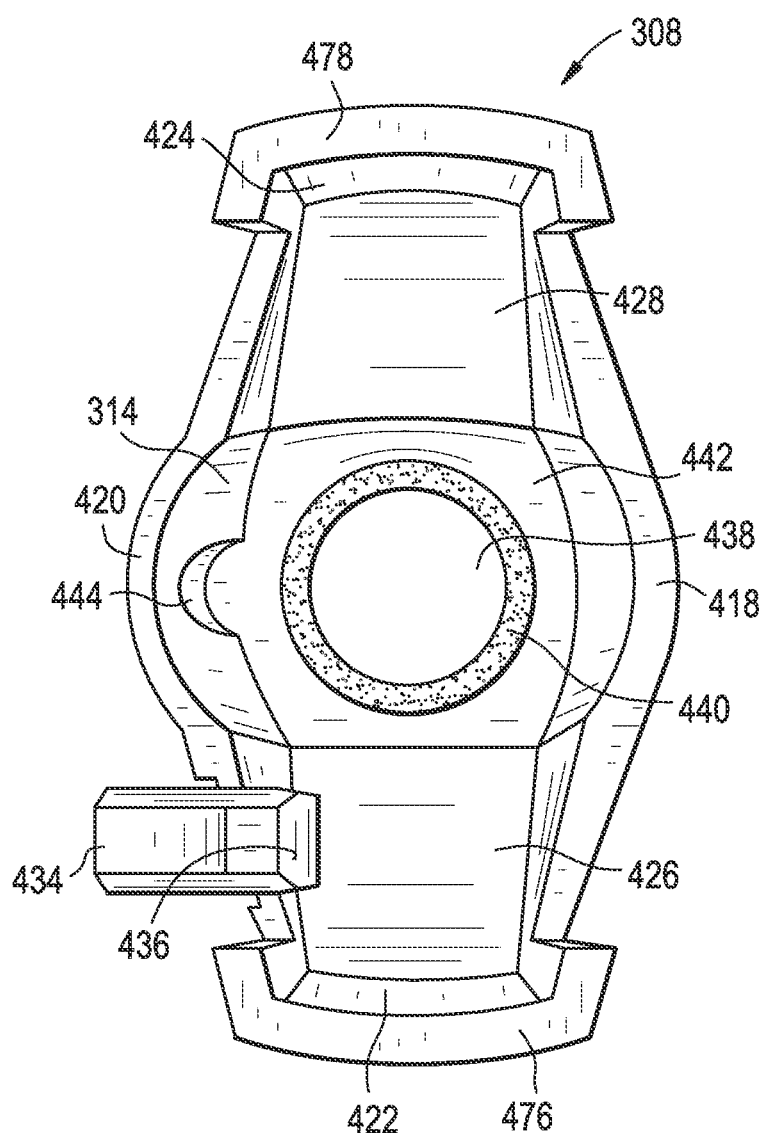
FIG. 7 is the spacer of the exemplary embodiment shown in FIG. 3.
Figure 8:
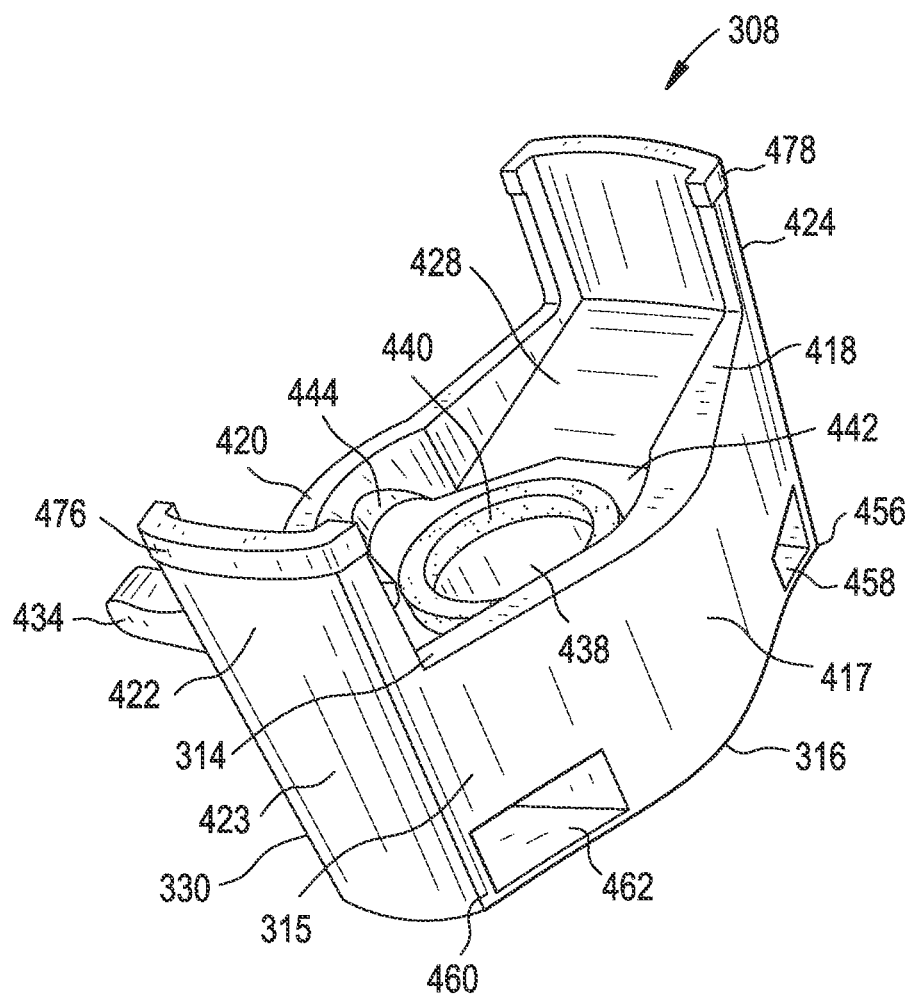
FIG. 8 is the spacer of the exemplary embodiment shown in FIG. 3.
Figure 9:
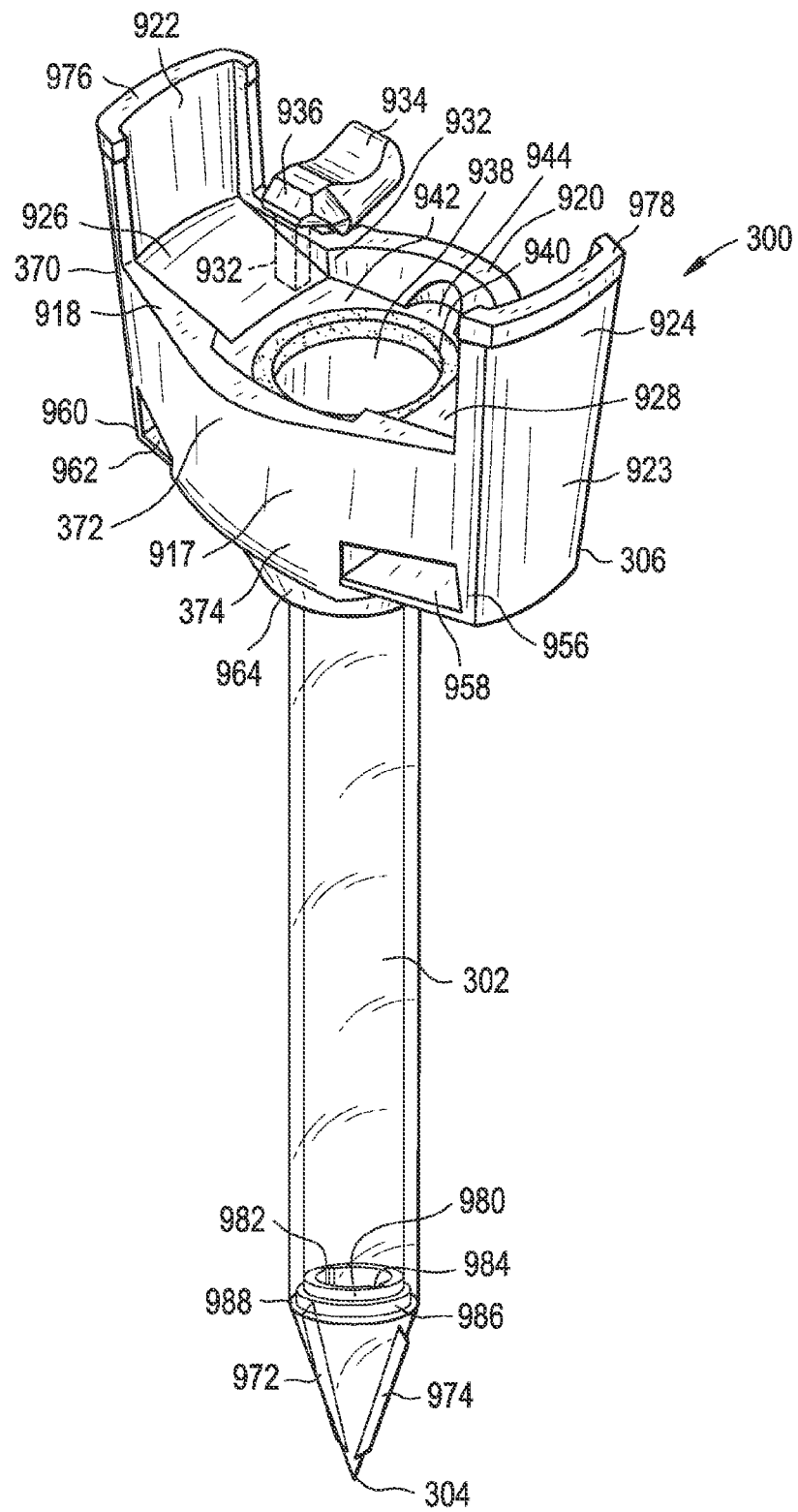
FIG. 9 is the device of the exemplary embodiment shown in FIG. 3 with a tab shown in a first position.

In some embodiments, spacer 308 may include a spacer lock configured to retain trocar main body 354 when spacer 308 receives trocar main body 354. The spacer lock may include any type of mechanism suitable for retaining trocar main body 354. For example, as shown in the exemplary embodiment of FIGS. 3-20, the spacer lock may include a tab 432. In some embodiments, tab 432 may be connected to spacer main body 330. Tab 432 may be connected to spacer main body 330 by any suitable mechanism. For example, as shown in the exemplary embodiment of FIGS. 2-20, tab may be connected to spacer main body 330 by being press fit into a spacer slot 670 disposed within fourth lateral surface 423. Tab 432 may include a lever 334. A tab tip 336 may be disposed opposite lever 334. Tab 432 may be made of a resilient material. For example, in some embodiments, tab 432 may be made of an elastomeric material or a resilient metal material. As shown in FIG. 5, the resilience of tab 432 may allow tab 432 to be pulled back by lever 334 so that tab tip 336 moves away from second top wall 420 and/or first sloped surface 426. This capability may allow tab tip 336 to be moved out of the way for trocar main body 354 to be received by spacer top portion 314, as shown in FIG. 5. When trocar main body 354 is in place on spacer top portion 314, lever 334 may be released so that tab tip 336 may lie over first trocar angled wall 352 of trocar main body portion 354, retaining trocar main body 354 on spacer top portion 314.

In some embodiments, the size, shape, and contour of spacer bottom portion 316 may be selected based on a variety of factors. For example, in some embodiments, spacer bottom portion 316 may be selected based on the type of trocar used with the system. In some embodiments, spacer bottom portion 316 may be configured to have a shape, size, and/or contour similar to the shape, size, and/or contour of the bottom portion of the trocar used with the system. In some embodiments, spacer bottom portion 316 may be configured to be received by a device top portion 370. In some embodiments, spacer bottom portion 316 may include a spacer central region 464 surrounding cylindrical spacer hole 438. In some embodiments, spacer central region 464 may be tapered toward cylindrical spacer hole 438. In some embodiments, spacer central region 464 may be cup-shaped. In some embodiments, a first bottom surface 466 may extend between spacer central region 464, first lateral surface 417, second lateral surface 619, and third lateral surface 621. In some embodiments, first bottom surface 466 may include a substantially flat surface. In some embodiments, a second bottom surface 468 may extend between spacer central region 464, first lateral surface 417, second lateral surface 619, and fourth lateral surface 423. In some embodiments, second bottom surface 468 may include a substantially flat surface.

In some embodiments, a first spacer angled wall 456 may extend between first bottom surface 466 and spacer central region 464. In some embodiments, first spacer angled wall 456 may extend between third lateral surface 621 and spacer central region 464. In some embodiments, a portion of first spacer angled wall 456 may be coincident with third lateral surface 621. In some embodiments, spacer bottom portion 316 may include a first spacer opening 458. In some embodiments, first spacer opening 458 may be defined by an inner surface of first spacer angled wall 456, first bottom surface 466, and a portion of spacer central region 464.

In some embodiments, a second spacer angled wall 460 may extend between second bottom surface 468 and the bottom of spacer central region 464. In some embodiments, second spacer angled wall 460 may extend between fourth lateral surface 423 and spacer central region 464. In some embodiments, a portion of second spacer angled wall 460 may be coincident with fourth lateral surface 423. In some embodiments, spacer bottom portion 316 may include a second spacer opening 462. In some embodiments, second spacer opening 462 may be defined by an inner surface of second spacer angled wall 460, second bottom surface 468, and spacer central region 464.

In some embodiments, device main body 306 may include a device top portion 370 and a device bottom portion 374. In some embodiments, device main body 306 may have a device middle portion 372 disposed between device top portion 370 and device bottom portion 374. In some embodiments, device middle portion 372 may include a first lateral surface 917 extending between device top portion 370 and device bottom portion 374. A second lateral surface 1119 may oppose first lateral surface 917 in a position extending between device top portion 370 and device bottom portion 374. A third lateral surface 1121 may extend between first lateral surface 917, second lateral surface 1119, device top portion 370, and device bottom portion 374. A fourth lateral surface 923 may extend between first lateral surface 917, second lateral surface 1119, device top portion 370, and device bottom portion 374. Fourth lateral surface 923 may oppose third lateral surface 1121. In some embodiments, first lateral surface 917 may be substantially curved. In some embodiments, second lateral surface 1119 may be substantially curved. In some embodiments, first lateral surface 917 and second lateral surface 1119 may both be substantially curved so that the distance between first lateral surface 917 and second lateral surface 1119 increases toward the middle of first lateral surface 917 and second lateral surface 1119.

In some embodiments, first lateral surface 917 may be substantially wider than third lateral surface 1121 and fourth lateral surface 923. In some embodiments, second lateral surface 1119 may be substantially wider than third lateral surface 1121 and fourth lateral surface 923. In some embodiments, first lateral surface 917 and second lateral surface 1119 may have substantially the same width. In some embodiments, the width of first lateral surface 917, second lateral surface 1119, third lateral surface 1121, and/or fourth lateral surface 923 may be tapered toward device bottom portion 374 (see FIG. 11). The width, shape, and contour of first lateral surface 917, second lateral surface 1119, third lateral surface 1121, and/or fourth lateral surface 923 may be selected based on a variety of factors. For example, the width, shape, and contours of the lateral surfaces may be selected based on how spacer 308 may nest with device 300. In some embodiments, first lateral surface 917, second lateral surface 1119, third lateral surface 1121, and/or fourth lateral surface 923 may have the same height. In some embodiments, first lateral surface 917, second lateral surface 1119, third lateral surface 1121, and fourth lateral surface 923 may have different heights. The height of first lateral surface 917, second lateral surface 1119, third lateral surface 1121, and/or fourth lateral surface 923 may be selected based on a variety of factors. For example, the height of the lateral surfaces may be selected based on the length of trocar sleeve 320, the length of device sleeve 302, and/or the size of spacer main body 330.

Device main body 306 defines a device aperture or device hole 938 that is in communication with sleeve 302. In some embodiments, a device hole 938 may extend through device main body 306. Device hole 938 may extend through the center of device top portion 370, continuing through the center of device middle portion 372 and the center of device bottom portion 374. In some embodiments, device hole 938 may include any size and/or shape, and may be eccentrically positioned on the device top portion. For example, as shown in the exemplary embodiment of FIGS. 3-20, device hole 938 may be cylindrical. In some embodiments, device hole 938 may be configured to receive obturator tube 340 and/or trocar sleeve 320. In some embodiments, the size and/or shape of device hole 938 may be selected based on a variety of factors. For example, in some embodiments, the size and/or shape of device hole 938 may be selected based on the size and/or shape of the tubes and sleeves device hole 938 is configured to receive. In some embodiments, device hole 938 may be configured to align with spacer hole 438 when device 300 and spacer 308 are assembled together.

In some embodiments, device top portion 370 may be configured to receive spacer main body 330. In some embodiments, device top portion 370 may be configured to receive a device bottom portion 374 of spacer main body 330. In some embodiments, device top portion 370 may have a shape corresponding to the shape of trocar bottom portion 346 of trocar main body 354. In some embodiments, device top portion 370 may have a shape corresponding to the shape of spacer bottom portion 316. The size, shape, and/or contour of device top portion 370 may be selected based on a variety of factors. For example, size, shape, and/or contour of device top portion 370 may be selected based on the type of trocar main body used with the system.

In some embodiments, device top portion 370 may include a first top wall 918 disposed along a section of the perimeter of device top portion 370 and a second top wall 920 disposed along a section of the perimeter of device top portion 370 opposite first top wall 918. In some embodiments, an outer surface of first top wall 918 may coincide with first lateral surface 917. In some embodiments, an outer surface of second top wall 920 may coincide with second lateral surface 1119. In some embodiments, an outer surface of third top wall 922 may coincide with third lateral surface 1121. In some embodiments, an outer surface of fourth top wall 934 may coincide with fourth lateral surface 923.

In some embodiments, the section of the perimeter of device top portion 370 that is coincident with first top wall 918 may include a substantially curved shape. In some embodiments, the section of the perimeter of device top portion 370 that is coincident with second top wall 920 may include a substantially curved shape. In some embodiments, the sections of the perimeter of device top portion 370 that are coincident with first top wall 918 and second top wall 920 may both be substantially curved so that the distance between first top wall 918 and second top wall 920 increases toward the middle of first top wall and second top wall (see FIG. 12).

In some embodiments, a third top wall 922 may extend between first top wall 918 and second top wall 920. Third top wall 922 may be disposed along a section of the perimeter of device top portion 370. In some embodiments, a fourth top wall 934 may extend between first top wall 918 and second top wall 920. Fourth top wall 934 may be disposed along a section of the perimeter of device top portion 370. In some embodiments, fourth top wall 934 may oppose third top wall 922. In some embodiments, the section of the perimeter of device top portion 370 that is coincident with third top wall 922 may include a slightly curved shape. In some embodiments, the section of the perimeter of device top portion 370 that is coincident with second top wall 324 may include a slightly curved shape. In some embodiments, third top wall 922 and fourth top wall 934 may both be substantially taller than first top wall 918 and second top wall 920. In some embodiments, first top wall 918 and second top wall 920 may be substantially wider than both third top wall 922 and fourth top wall 934. In some embodiments, third top wall 922 may include a first flange 976 and fourth top wall 934 may include a second flange 978.

In some embodiments, device top portion 370 may be configured to receive a trocar bottom portion 346 of a trocar main body 354 such that trocar main body nests within the space between first top wall 918, second top wall 920, third top wall 922, and fourth top wall 934 (FIG. 16). In some embodiments, device 300 may be configured such that trocar bottom portion 346 of trocar main body 354 may fit flush within the space between first top wall 918, second top wall 920, third top wall 922, and fourth top wall 934. In some embodiments, device top portion 370 may be configured to receive a spacer bottom portion 316 such that spacer main body 330 nests within the space between first top wall 918, second top wall 920, third top wall 922, and fourth top wall 934 (FIG. 16). In some embodiments, device 300 may be configured such that spacer bottom portion 316 may fit flush within the space between first top wall 918, second top wall 920, third top wall 922, and fourth top wall 934.

In some embodiments, device top portion 370 may include a first sloped surface 926 and a second sloped surface 928 opposing first sloped surface 926. First sloped surface 926 may be disposed between first top wall 918, second top wall 920, third top wall 922, and device hole 938. Second sloped surface 928 may be disposed between first top wall 918, second top wall 920, fourth top wall 934, and device hole 938. In some embodiments, first sloped surface 926 and second sloped surface 928 may both decline toward the center of device top portion 370. In some embodiments, first sloped surface 926 and second sloped surface 928 may both include flat surfaces declining toward the center of device top portion 370.

In some embodiments, first sloped surface 926 may be configured to receive first trocar angled wall 352 disposed on trocar bottom portion 346. In some embodiments, first sloped surface 926 may be configured to receive first spacer angled wall 456. In some embodiments, second sloped surface 928 may be configured to receive a second trocar angled wall (not shown) of trocar bottom portion 346, which is a mirror image of first trocar angled wall 352. In some embodiments, second sloped surface 928 may be configured to receive second spacer angled wall 460. In some embodiments, third top wall 922 and fourth top wall 934 may be configured to receive trocar bottom portion 346. In some embodiments, third top wall 922 and fourth top wall 934 may be configured to receive spacer bottom portion 316. In some embodiments, third top wall 922 may be configured to receive a first trocar angled wall 352 disposed on trocar bottom portion 346. In some embodiments, third top wall 922 may be configured to receive a first spacer angled wall 456. In some embodiments, fourth top wall 934 may be configured to receive the second trocar angled wall (not shown) of trocar main body 354. In some embodiments, fourth top wall 934 may be configured to receive the second spacer angled wall 460.

In some embodiments, a washer space may surround device hole 938. Washer space may be configured to receive a washer 940 surrounding device hole 938. In some embodiments, the washer space may include an annular groove having a shape corresponding to the shape of washer 940. In some embodiments, washer 940 may be configured to seal the area between a trocar sleeve 320 and device hole 938 when trocar 310 is assembled with device 300. In some embodiments, washer 940 may be configured to seal the area between spacer hole 438 and device hole 938 when trocar 310 is assembled with device 300.

In some embodiments, a recessed area 942 may surround the washer space. In some embodiments, recessed area 942 may be configured to receive trocar bottom portion 346. In some embodiments, recessed area 942 may be configured to receive spacer bottom portion 316. In some embodiments, recessed area 942 may include a surface declining toward the washer space. In some embodiments, recessed area 942 may include a flat surface. In some embodiments, recessed area 942 may be disposed between first sloped surface 926 and second sloped surface 928. In some embodiments, recessed area 942 may be disposed between first top wall 918 and second top wall 920. In some embodiments, recessed area 942 may be configured to correspond with the substantially cup-shaped area 348 on trocar bottom portion 346. In some embodiments, recessed area 942 may be configured to correspond with spacer central region 464. In some embodiments, recessed area 942 may include a semicircular nook 944. In some embodiments, semicircular nook 944 may be configured to correspond with a semicircular protrusion disposed on trocar bottom portion 346. In some embodiments, semicircular nook 944 may be configured to correspond with a semicircular protrusion disposed on spacer bottom portion 316.

In some embodiments, device 300 may include a device lock configured to retain trocar main body 354 when device 300 receives trocar main body 354 and/or to retain spacer main body 330 when device 300 receives spacer main body 330. The device lock may include any type of mechanism suitable for retaining trocar main body 354 and/or spacer main body 330. For example, as shown in the exemplary embodiment of FIGS. 3-20, the device lock may include a tab 932. In some embodiments, tab 932 may be connected to device main body 306. Tab 932 may be connected to device main body 306 by any suitable mechanism. For example, as shown in the exemplary embodiment of FIGS. 3-20, tab may be connected to device main body 306 by being press fit into a device slot 1130 disposed within fourth lateral surface 923. Tab 932 may include a lever 934. A tab tip 936 may be disposed opposite lever 934.

Figure 10:
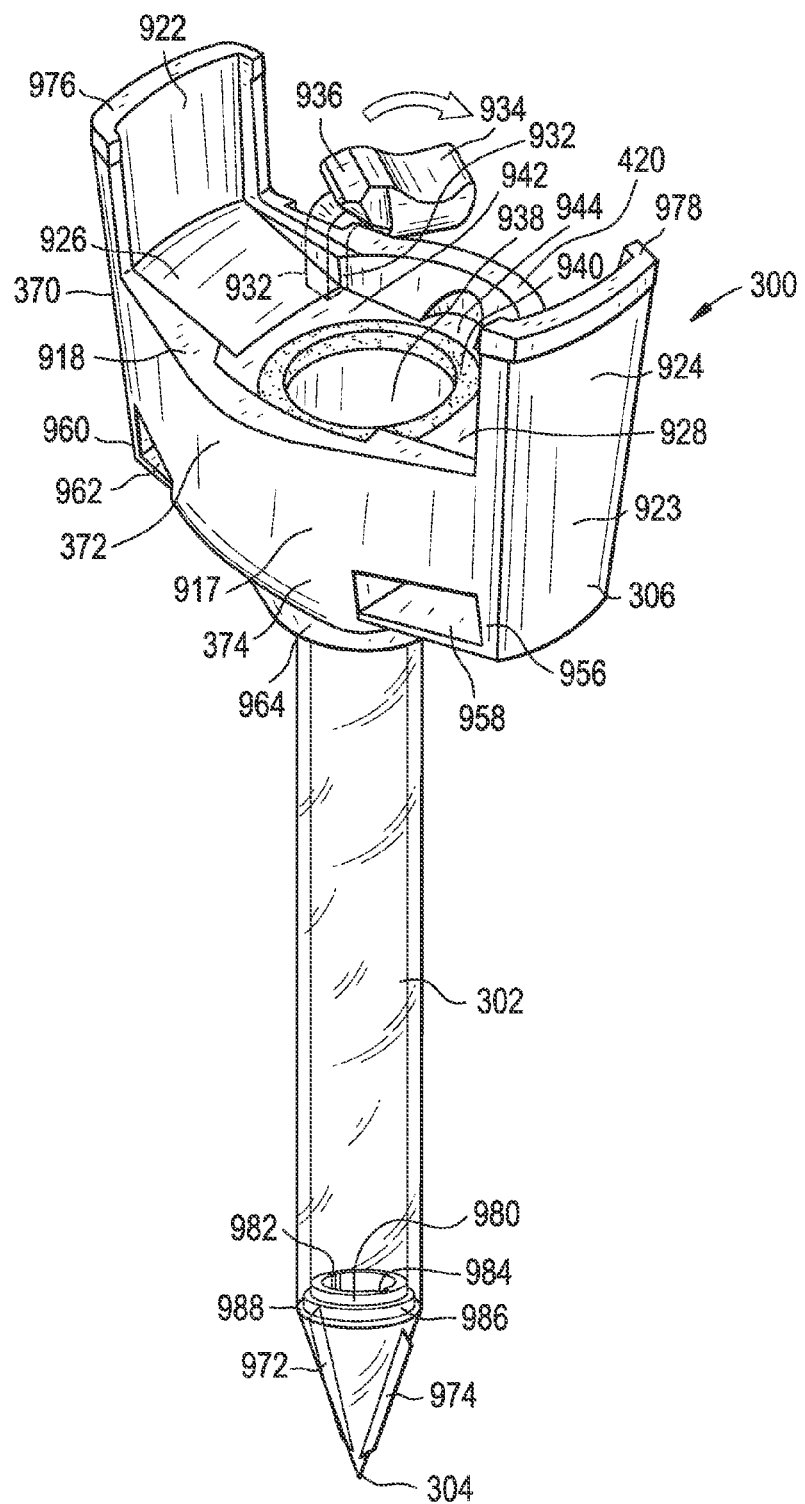
FIG. 10 is the device of the exemplary embodiment shown in FIG. 3 with the tab shown in a second position.
Figure 11:
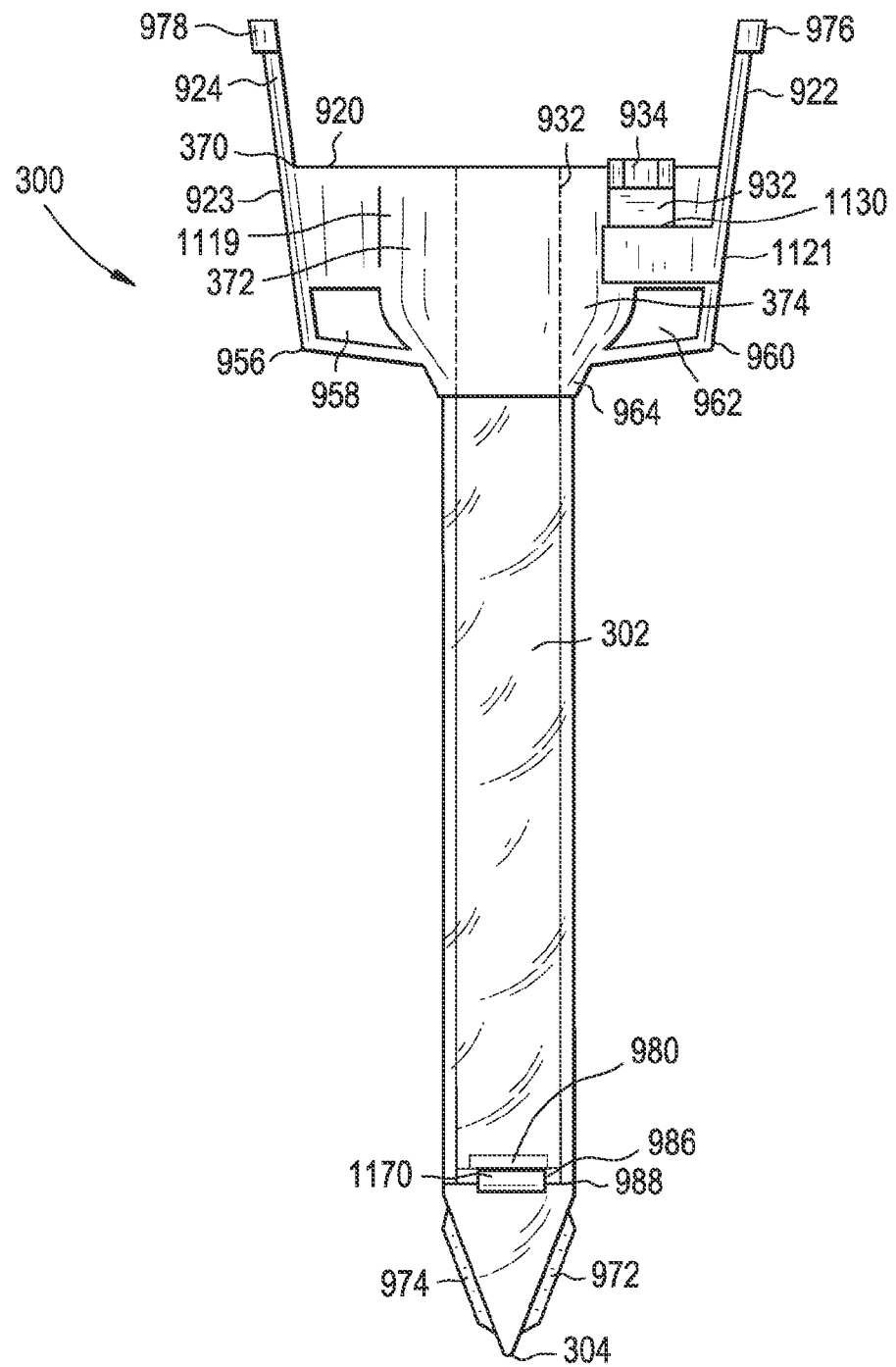
FIG. 11 is the device of the exemplary embodiment shown in FIG. 3.
Figure 12:
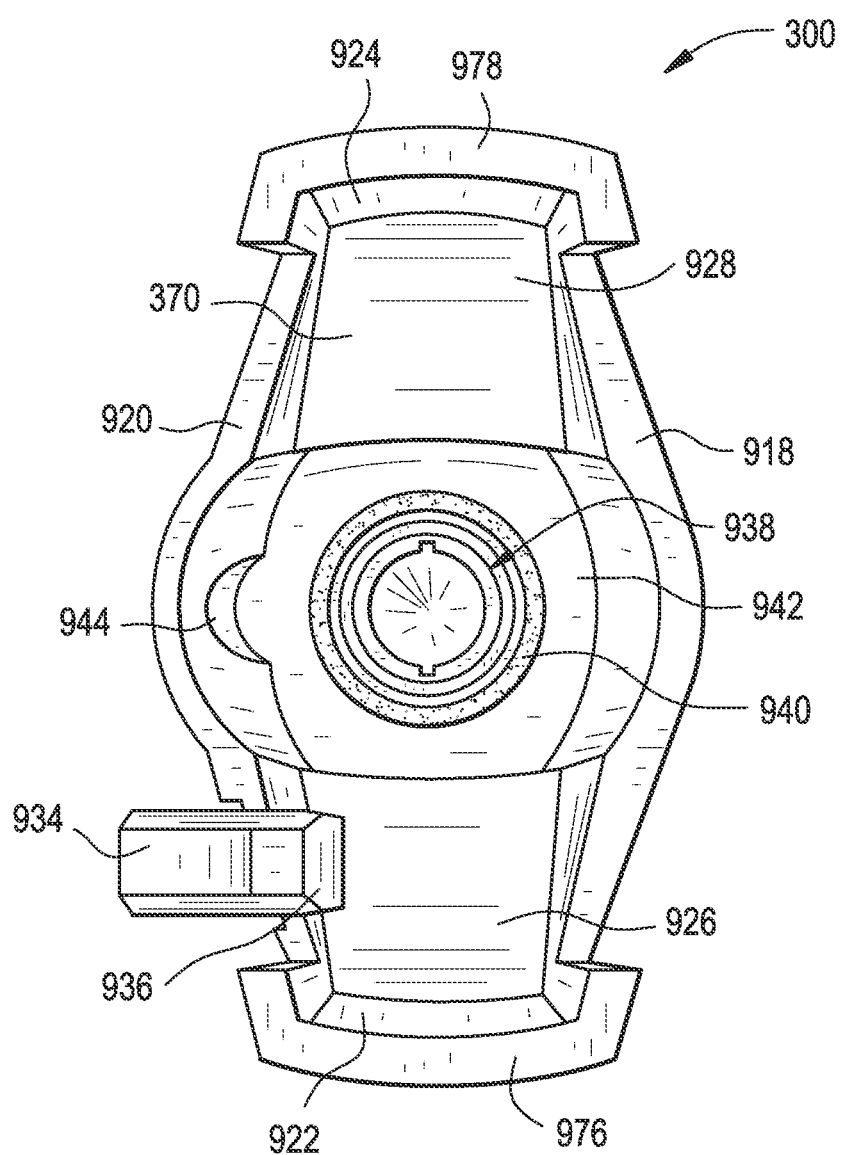
FIG. 12 is the device of the exemplary embodiment shown in FIG. 3.
Figure 13:
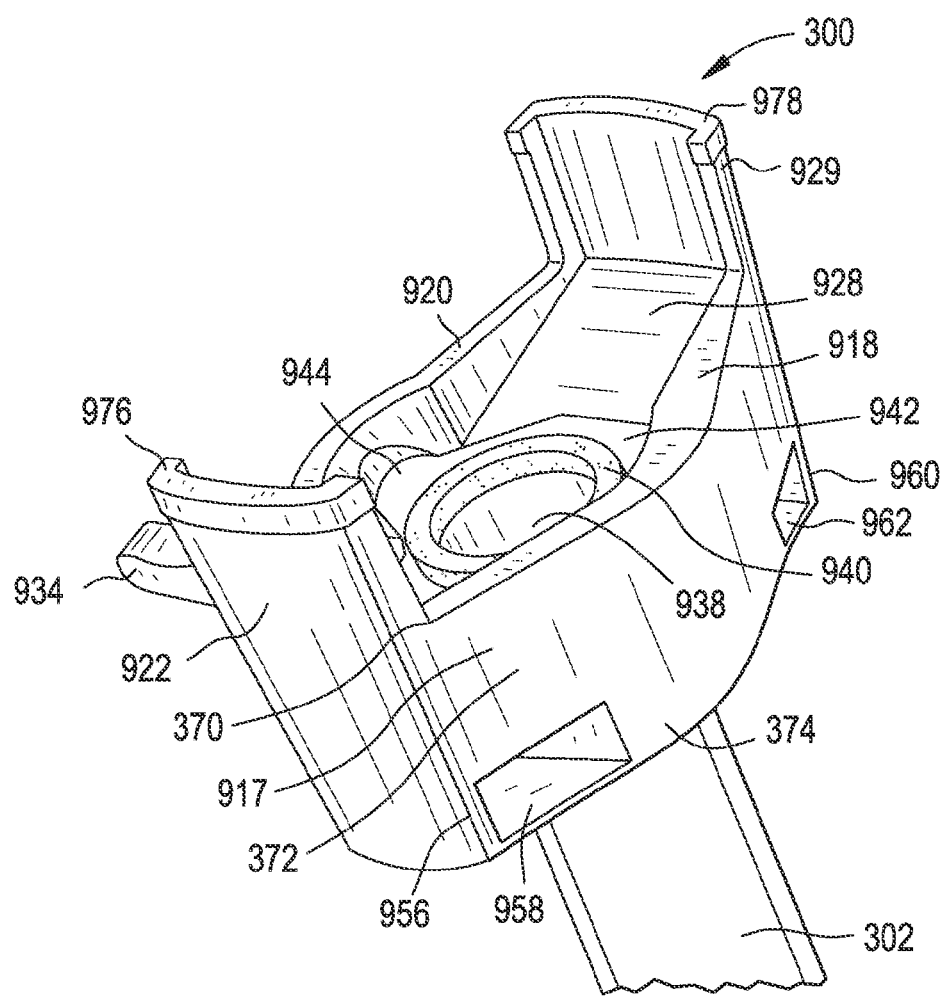
FIG. 13 is a main body portion and the proximal end of a sleeve of the device of the exemplary embodiment shown in FIG. 3.
Figure 14:
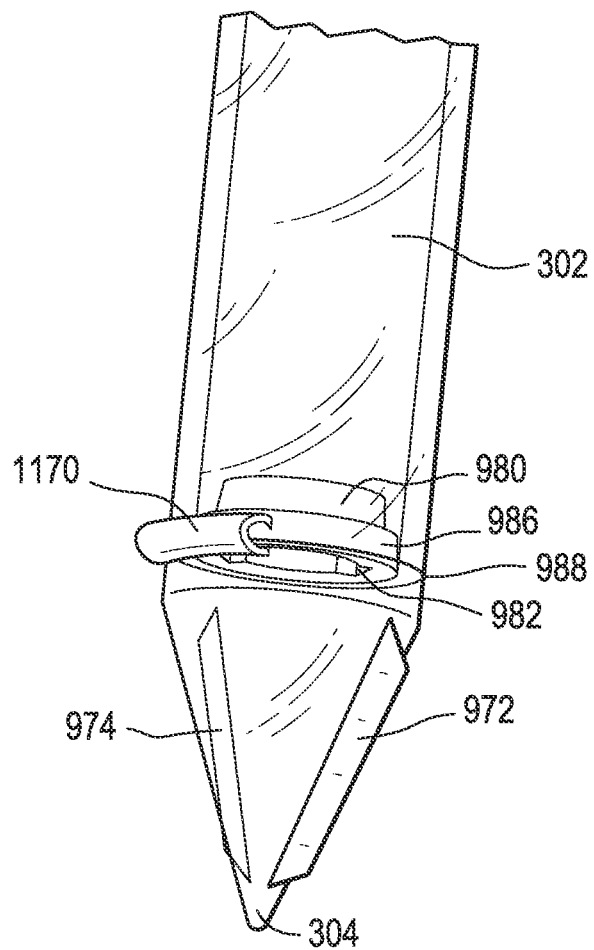
FIG. 14 is the distal end of the sleeve of the device of the exemplary embodiment shown in FIG. 3 with a device pointed tip removed from the distal end of the sleeve.

Tab 932 may be made of a resilient material. For example, in some embodiments, tab 932 may be made of an elastomeric material or a resilient metal material. As shown in FIG. 10, the resilience of tab 932 may allow tab 932 to be pulled back by lever 934 so that tab tip 936 moves away from second top wall 920 and/or first sloped surface 926. This capability may allow tab tip 936 to be moved out of the way for trocar main body 354 and/or spacer main body 330 to be received by device top portion 370, as shown in FIG. 10. Thus, when trocar main body 354 is in place on device top portion 370, lever 934 may be released so that tab tip 936 may lie over first trocar angled wall 352 of trocar main body 354, retaining trocar main body 354 on device top portion 370. When spacer main body 330 is in place on device top portion 370, lever 934 may be released so that tab tip 936 may lie over first spacer angled wall 456, retaining spacer main body 330 on device top portion 370.

In some embodiments, the size, shape, and contour of device bottom portion 374 may be selected based on a variety of factors. For example, in some embodiments, device bottom portion 374 may be selected based on the type of trocar used with the system and/or the material of device main body 306. In some embodiments, device bottom portion 374 may be configured to have a shape, size, and/or contour similar to the shape, size, and/or contour of the bottom portion of the trocar used with the system. In some embodiments, device bottom portion 374 may include a device central region 964 surrounding cylindrical device hole 938. In some embodiments, device central region 964 may be tapered toward cylindrical device hole 938. In some embodiments, device central region 964 may be cup-shaped. In some embodiments, a first bottom surface 966 may extend between device central region 964, first lateral surface 917, second lateral surface 1119, and third lateral surface 1121. In some embodiments, first bottom surface 966 may include a substantially flat surface. In some embodiments, a second bottom surface 968 may extend between device central region 964, first lateral surface 917, second lateral surface 1119, and fourth lateral surface 923. In some embodiments, second bottom surface 968 may include a substantially flat surface.

In some embodiments, a first device angled wall 956 may extend between first bottom surface 966 and device central region 964. In some embodiments, first device angled wall 956 may extend between third lateral surface 1121 and device central region 964. In some embodiments, a portion of first angled wall 956 may be coincident with third lateral surface 1121. In some embodiments, device bottom portion 374 may include a first device opening 958. In some embodiments, first device opening 958 may be defined by an inner surface of first device angled wall 956, first bottom surface 966, and device central region 964.

In some embodiments, a second device angled wall 960 may extend between second bottom surface 968 and device central region 964. In some embodiments, second device angled wall 960 may extend between fourth lateral surface 923 and the bottom of device central region 964. In some embodiments, a portion of second device angled wall 960 may be coincident with fourth lateral surface 923. In some embodiments, device bottom portion 374 may include a second device opening 962. In some embodiments, second device opening 962 may be defined by an inner surface of second device angled wall 960, second bottom surface 968, and a portion of device central region 964.

In some embodiments, device sleeve 302 may be disposed on device bottom portion 374. In some embodiments, device sleeve 302 may be disposed adjacent device central region 964. In some embodiments, device sleeve 302 may extend from device central region 964 such that device hole 938 may continue through device sleeve 302. The distal end of device sleeve 302 may include a device sleeve open end 988.

Device pointed tip 304 may include any suitable shape. For example, as shown in the exemplary embodiment of FIGS. 3-20, device pointed tip 304 may include a substantially conical shape. In some embodiments, device pointed tip 304 may include a single piece that tapers from a proximal end to a distal end. In some embodiments, device pointed tip 304 may be substantially solid. In some embodiments, device pointed tip 304 may be substantially hollow. The size, shape, and contour of device pointed tip 304 may be selected based upon a variety of factors. For example, the size, shape, and contour of device pointed tip 304 may be selected based on the size, shape, and contour of an obturator pointed tip 318. In another example, the size, shape, and contour of device pointed tip 304 may be selected to facilitate navigating through a body cavity.

In some embodiments, device pointed tip 304 may include a provisions for facilitating separating tissue as device pointed tip 304 is pressed through the body cavity. For example, as shown in the exemplary embodiment of FIGS. 3-20, device pointed tip 304 may include a first device separator 972 and a second device separator 974. In some embodiments, first device separator 972 and second device separator 974 may be integrally formed with device pointed tip 304. In some embodiments, first device separator 972 and second device separator 974 may be connected to device pointed tip 304 by any known method. For example, first device separator 972 and second device separator 974 may be connected to device pointed tip 304 by adhesive.

First device separator 972 and second device separator 974 may include blades disposed on the exterior sides of device pointed tip 304. The size, shape, and/or contours of separators may be selected based on a variety of factors. For example, the size, shape, and/or contours of separators may be selected based on the size and/or shape of device pointed tip 304. In some embodiments, first device separator 972 may be disposed opposite second device separator 974. In other embodiments, the separators may be disposed on the sides of device pointed tip 304 in other locations. While the exemplary embodiment of FIGS. 3-20 includes two separators, device pointed tip 304 may include any number of separators. For example, in some embodiments, device pointed tip 304 may include one separator. In other embodiments, device pointed tip 304 may include between two and six separators. In other embodiments, device pointed tip 304 may include between five and ten separators. In other embodiments, device pointed tip 304 may include between nine and twenty separators. The number of separators may be selected based on a variety of factors. For example, the number of separators may be selected based on the size and/or shape of device pointed tip 304.

Device pointed tip 304 may be disposed on the distal end of device sleeve 302. In some embodiments, device pointed tip 304 may be connected to the distal end of device sleeve 302 by a hinge 1170. Hinge 1170 may include any suitable type of hinge. For example, hinge 1170 may include a slot and pin hinge. As shown in the exemplary embodiment of FIGS. 3-20, hinge 1170 may include a living hinge. Hinge 1170 may a thin web of flexible material allowing device pointed tip 304 to change positions. For example, in a first position, device pointed tip 304 may point downward away from the proximal end of device sleeve 302 (FIGS. 9-11, 14, 15, and 20) and, in a second position, device pointed tip 304 may point laterally with respect to the longitudinal axis of device sleeve 302 (FIGS. 17-19). The positions of device pointed tip 304 are discussed in further detail with reference to FIGS. 16-20 below. The size, shape, material, and/or location of hinge 1170 may be selected based on a variety of factors. For example, the size, shape, material, and/or location may be selected based on the type of material used to make device 300, the dimensions of device 300, and/or the type of trocar to be used with the system.

Figure 15:
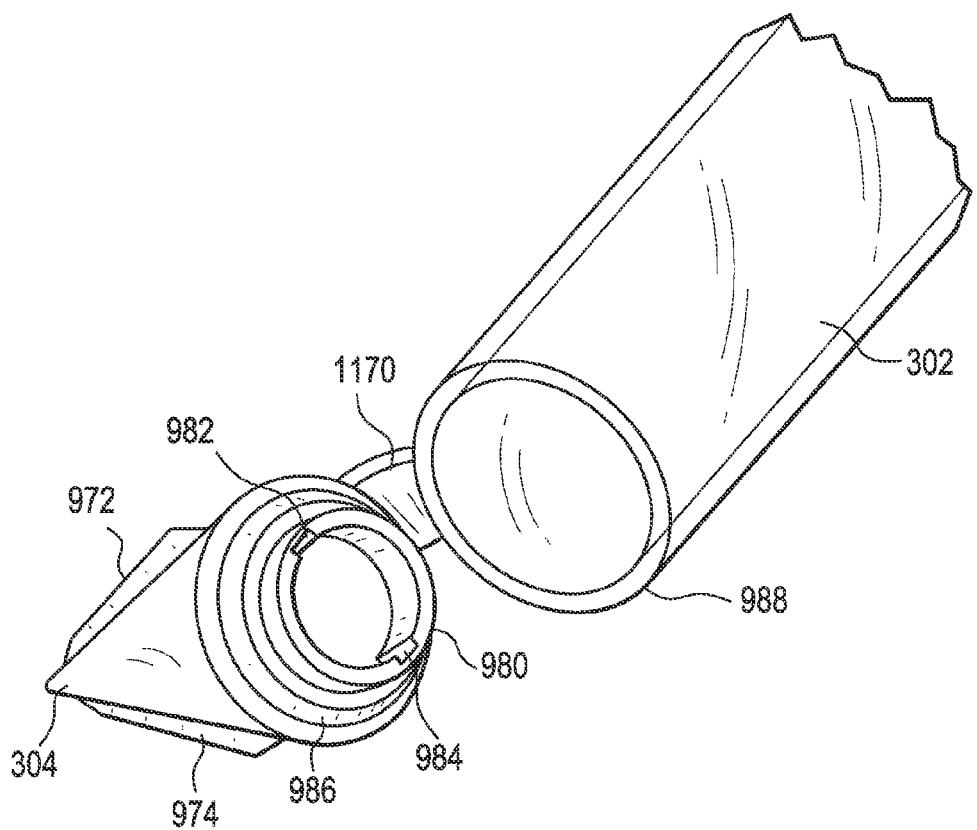
FIG. 15 is the distal end of the sleeve of the device of the exemplary embodiment shown in FIG. 3 with a first lip of the device pointed tip disposed within the distal end of the sleeve.

In some embodiments, device pointed tip 304 may include a mechanism capable of retaining device pointed tip 304 within the distal end of sleeve 302 (FIG. 15). For example, as shown in the exemplary embodiment of FIGS. 3-20, device pointed tip 304 may include a first lip 986. First lip 986 may be disposed on the interior surface of the proximal end of device pointed tip 304. In some embodiments, first lip 986 may have a shape corresponding to the shape of device sleeve open end 988. For example, as shown in the exemplary embodiment of FIGS. 3-20, first lip 986 may have an annular shape. In some embodiments, first lip 986 may have an outer dimension substantially similar to the inner dimension of device sleeve open end 988. For example, first lip 986 may have an outer diameter substantially similar to the inner diameter of device sleeve open end 988. In some embodiments, first lip 986 may fit flush within the distal end of device sleeve 302 such that first lip 986 may be retained within device sleeve open end 988 by friction between first lip 986 and device sleeve open end 988. Thus, when first lip 986 is pushed into device sleeve open end 988 (FIGS. 9-11 and 14), first lip 986 may be retained in a first position within device sleeve open end 988. Device pointed tip 304 may close device sleeve open end 988 in the first position.

In some embodiments, device pointed tip 304 may include an interior portion on its proximal end that is sized and shaped to correspond with the exterior surface of obturator pointed tip 318. In some embodiments, the interior portion may be configured to receive and/or secure the exterior surface of obturator pointed tip 318. In some embodiments, the interior portion of device pointed tip 304 may be configured to cause device pointed tip 304 to be pushed to the second position when trocar sleeve 320 is inserted in device sleeve 302, as discussed in more detail below with reference to FIG. 17. The interior portion of device pointed tip 304 may include a second lip 980 disposed on the interior surface of the proximal end of device pointed tip 304. In some embodiments, second lip 980 may be disposed adjacent first lip 986. In some embodiments, the size, shape, and contours of second lip 980 may be selected based on a variety of factors. For example, the size, shape, and contours of second lip 980 may be selected based on the size, shape, and contours of obturator pointed tip 318 and trocar sleeve 320. In some embodiments, second lip 980 may have an annular shape. In some embodiments, second lip 980 may include a first notch 982 and a second notch 984. In some embodiments, second notch 984 may be disposed opposite first notch 982. First notch 982 may be configured to receive a first obturator separator 372. Second notch 984 may be configured to receive second obturator separator 374. The size, shape, and/or contours of first notch 982 and second notch 984 may be selected based on a variety of factors. For example, the size, shape, and/or contours of first notch 982 may be selected based on the size, shape, and/or contours of first obturator separator 372. The size, shape, and/or contours of second notch 984 may be selected based on the size, shape, and/or contours of second obturator separator 374. While the exemplary embodiment of FIGS. 3-20 shows two notches, second lip 980 may include any number of notches. For example, in some embodiments, second lip 980 may include between three and five notches. The number of notches may be selected based on a variety for factors. For example, the number of notches may be selected based on the number of separators disposed on the obturator tip used with the system.

FIG. 16 illustrates how device 300, spacer 308, trocar 310, and obturator 312 may be assembled and secured together. In some embodiments, trocar 310 may be retained within spacer top portion 314 by tab 432. In some embodiments, spacer bottom portion 316 may be retained within device top portion 370 by tab 932. In some embodiments, device pointed tip 304 may be retained in device sleeve open end 988. Device pointed tip 304 may be retained in device sleeve open end 988 in a first position in which device pointed tip 304 is directed downward away from a proximal end of sleeve 302. In some embodiments, first lip 986 may retain device pointed tip 304 in opening 988. Disposed between device 300 and obturator 312, spacer 308 and trocar 310 may position obturator 312 such that an obturator pointed tip 318 may rest upon second lip 980. First notch 982 may receive first obturator separator 372. Second notch 984 may receive a second obturator separator 374. Second lip 980 may secure obturator pointed tip 318 as device 300, spacer 308, trocar 310, and obturator 312 are inserted into the body cavity. Thus, pressure applied to obturator 312 may be transmitted to obturator pointed tip 318, and further transmitted to device pointed tip 304. During insertion through an incision, device pointed tip 304, first device separator 972, and second device separator 974 may be used to guide device sleeve 302 into the body cavity. First device separator 972 and second device separator 974 may help separate tissue as sleeve 302 is pressed and/or twisted into the body cavity. Once device 300 is positioned within the body cavity, obturator 312, trocar 310, and spacer 308 may be removed from device 300.

FIG. 17 illustrates how trocar 310 may be inserted within device 300. Device sleeve 302 may receive trocar sleeve 320. As trocar sleeve open end 322 is pushed against second lip 980, trocar sleeve open end 322 may push device pointed tip 304 out of device sleeve open end 988. As trocar sleeve 320 proceeds through device sleeve open end 988 open end, trocar sleeve open end 322 may push device pointed tip 304 to the second position. Device pointed tip 304 may pivot about hinge 1170 to a second position in which device pointed tip 304 is directed laterally with respect to the longitudinal axis of device sleeve 302. Trocar sleeve open end 322 may protrude through device sleeve open end 988. Trocar sleeve 320 may hold device pointed tip 304 in the second position as trocar sleeve open end 322 protrudes through device sleeve open end 988. Trocar sleeve 320 may prevent device pointed tip 304 from pointing in the first position.

FIG. 18 illustrates how trocar 310 may be assembled with device 300 while device 300 is positioned inside the body cavity. For example, device 300 may remain in the body cavity after the assembly of device 300, spacer 308, trocar 310, and obturator 312 shown in FIG. 16 has been inserted into the body cavity through an incision and spacer 308, trocar 310, and obturator 312 have been removed. While device 300 remains in the body cavity, trocar 310 may be assembled with device 300 as shown in FIG. 17. With this setup, carbon dioxide gas and/or a surgical instrument 1800 may be introduced into the body cavity via trocar sleeve 320. Surgical instrument 1800 may include a set of graspers having a grasping end 1802 that opens and closes. When grasping end 1802 is closed, surgical instrument 1800 may fit within device sleeve 302 and/or trocar sleeve 320. In some embodiments, surgical instrument 1800 may be inserted in and removed from device sleeve 302 and/or trocar sleeve 320 when grasping end 1802 is closed.

When grasping end 1802 is open, surgical instrument 1800 may not fit within device sleeve 302 and/or trocar sleeve 320. FIG. 19 illustrates grasping end 1802 being inadvertently pulled upward while grasping end 1802 is opened and positioned within the body cavity through device sleeve 302 and/or trocar sleeve 320. Because grasping end 1802 is opened, grasping end 1802 may get caught on device sleeve open end 988 as instrument 1800 is pulled upward. As a result, grasping end 1802 may push device 300 upward. FIG. 19 illustrates how device pointed tip 304 may anchor device 300 within the body cavity as grasping end 1802 pushes against device 300. As device 300 is pushed upward, device pointed tip 304 may be pressed against the internal peritoneal lining and/or tissues of the body cavity. The pressure against device pointed tip 304 may cause device pointed tip 304 to begin to pivot downward. However, the portion of trocar sleeve 302 protruding through device sleeve open end 988 may prevent device pointed tip 304 from pivoting to a position in which device pointed tip 304 points downward. Thus, device pointed tip 304 may remain against the internal peritoneal lining and/or tissues as device 300 is pushed upward. With device pointed tip 304 pointed laterally with respect to the longitudinal axis of device sleeve 302, device 300 may not fit through the incision through which device 300 was introduced into the body cavity. Thus, as shown in FIG. 19, removal of device 300 may be prevented when trocar sleeve 320 protrudes through device sleeve open end 988. In some embodiments, device 300 may be further secured within body cavity by suturing device 300 to the patient's skin adjacent the incision. In these embodiments, sutures may be looped through first device opening 958 and/or second device opening 962 to secure device 300 to the patient's skin.

FIG. 20 illustrates how device 300 may be removed from the body cavity. Without instrument 1800 or trocar 310 disposed within device sleeve 302, device pointed tip 304 may be allowed to pivot downward. As device 300 is pulled upward in the direction shown by the arrow in FIG. 20, tissues inside the body cavity and/or the internal peritoneal lining of the body cavity may press down on device point tip 304. The pressure may cause device pointed tip 304 to pivot such that device pointed tip 304 downward in a direction opposite device main body 306. In this position, device pointed tip 304 may fit through the incision through which device 300 was introduced into the body cavity. Thus, device 300 may be removed from the body cavity.

Device 300 and spacer 308 may be made of any suitable material. For example, device 300 and/or spacer 308 may be made from a plastic material. In some embodiments, device 300 and/or spacer 308 may be made of a biocompatible material. In some embodiments, device 300 and/or spacer 308 may be made of a transparent material. In some embodiments, device 300 and/or spacer 308 may be made of radio-opaque material. In some embodiments, device 300 and spacer 308 may be made of the same type of material. In other embodiments, device 300 and spacer 308 may be made of different types of materials. In some embodiments, device 300 may be made of multiple types of materials. For example, sleeve 302 may be made of a first material and device main body 306 may be made of a second material. In some embodiments, spacer 308 may be made of multiple types of materials. For example, main body 330 may be made of a first material and tab 432 may be made of a second material. The material of device 300 and/or spacer 308 may be selected based on a variety of factors. For example, the material of device 300 and/or spacer 308 may be selected based on the machining process used to make the components, the material of the trocar used with the system, and/or flexibility of the materials.

Any directional adjectives used in this description are used for simplicity with reference to the orientation of the device or elements as illustrated in the accompanying drawings. It will be understood that in use, a device such as the one described would be in different orientations depending on the procedure and the user. Accordingly, the invention is not to be restricted or interpreted to be limited to the illustrated orientations, but only in light of the claims and their equivalents.

While various embodiments of the invention have been described, the description is intended to be exemplary, rather than limiting and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

I claim:

1. A device for anchoring a trocar within a body cavity, comprising:
   a device main body defining a device aperture therethrough;
   a device sleeve extending from the device main body, the device sleeve having a proximal end and an open distal end and defining a sleeve aperture in communication with said device aperture;
   a device tip having a proximal end configured to be retained within the sleeve aperture at the open distal end of the device sleeve and a distal end opposite the proximal end; and
   the device tip being hingedly connected to the open distal end of the device sleeve such that the device tip may be moved from a first position in which the distal end of the device tip is aligned with the longitudinal axis of the device sleeve, to a second position in which the distal end of the device tip is angled with respect to the longitudinal axis of the device sleeve.

2. The device according to claim 1, wherein the device sleeve is configured to receive a trocar sleeve and the device tip is configured to move from the first position to the second position by the distal end of the trocar sleeve inserted into the device sleeve.

3. The device according to claim 2, wherein the device tip is configured to be held in the second position by the trocar sleeve when the trocar sleeve is inserted into the device sleeve and protrudes from the open distal end of the device sleeve.

4. The device according to claim 1, wherein the device tip includes a single piece forming a substantially conical shape.

5. The device according to claim 4, wherein the device tip includes at least one separator disposed on an exterior surface of the device tip.

6. The device according to claim 1, wherein an interior portion of the device tip includes an annular lip configured to be received by the open distal end of the device sleeve to retain the annular lip within the open distal end.

7. The device according to claim 6, wherein the device sleeve is configured to receive a trocar sleeve and the annular lip is configured to be moved by the distal end of a trocar sleeve inserted into the device sleeve.

8. The device according to claim 1, wherein the top portion is configured to receive a trocar main body and the top portion includes a retaining tab configured to retain the trocar main body on the top portion.

9. The device according to claim 1, further comprising a spacer having a first surface configured to connectedly attach to a trocar main body, and a second surface configured to attach to the device main body, said spacer defining a spacer aperture in communication with said main body aperture when the spacer is assembled to the device, said spacer aperture configured to receive the trocar main body.

10. A device for anchoring a trocar within a body cavity, comprising:
    a device main body having a top surface and a bottom surface opposite the top surface, said device main body defining a main body aperture therethrough;
    a device sleeve defining a sleeve aperture in communication with said main body aperture, the sleeve aperture and the main body aperture both being configured to receive an obturator tube having a cone-shaped distal end, the device sleeve having its proximal end attached to and extending from the device main body bottom surface, and an open distal end; and
    a device tip hingedly connected to the distal end of said device sleeve and having a proximal end with a first lip configured to receive the obturator tip having a substantially conical tip within the first lip, wherein the proximal end of the device tip is configured to be retained within the sleeve aperture.

11. The device according to claim 10, wherein the device tip comprises a single piece, substantially conical shaped element.

12. The device according to claim 10, wherein the top surface has a recess configured to receive a trocar main body.

13. The device according to claim 12, wherein the first lip is configured to receive an obturator tip having at least one separator and the first lip includes at least one notch configured to receive the at least one separator.

14. The device according to claim 10, wherein the first lip is annular and is configured to receive an obturator tip having a first separator and a second separator and wherein the first lip includes a first notch and a second notch, the first notch configured to receive the first separator and the second notch configured to receive the second separator.

15. The device according to claim 14, wherein the proximal end of the device tip includes a second lip configured to be received by the open distal end of the device sleeve to retain the device tip on the open distal end of the device sleeve.

16. The device according to claim 12, wherein the proximal end of the device tip includes a second lip configured to be received by the open distal end of the device sleeve to retain the device tip on the open distal end of the device sleeve.

17. The device according to claim 16, wherein the proximal end of the device tip includes a hinge connecting the proximal end of the device tip to the open distal end of the device sleeve.

18. The device according to claim 10, further comprising a spacer having a first surface configured to connectedly attach to a trocar main body, and a second surface configured to attach to the device main body, said spacer defining a spacer aperture in communication with said main body aperture when the spacer is assembled to the device, said spacer aperture configured to receive the trocar main body.

19. A device for anchoring a trocar within a body cavity, comprising:
    a device main body defining a main body aperture configured to receive a trocar sleeve;
    a device sleeve having an attachment end and an open free end and defining a sleeve aperture, said device sleeve attached to said device main body such that said main body aperture and sleeve aperture are in communication and configured together to receive a trocar sleeve;
    a device tip having a proximal end movably attached to the free end of said device sleeve such that the device tip is movable from a first position in which said device tip is aligned with respect to the longitudinal axis of said device sleeve, to a second position in which said device tip is angled with respect to the longitudinal axis of said device sleeve, and wherein the proximal end of the device tip has an annular lip configured to be retained within the device sleeve aperture; and
    a hinge connecting said device tip to the open end of said device sleeve, the hinge providing pivotable movement between the first position and the second position.

20. The device according to claim 19, further comprising:
    a spacer defining a spacer aperture in communication with said main body aperture, said spacer having a spacer first surface and a spacer second surface opposite the spacer first surface, the spacer first surface configured to engage the trocar and the spacer second surface configured to attached to the device main body, wherein the device main body has a recess configured to receive the spacer second surface.

* * * * *